(12) United States Patent
Anderson et al.

(10) Patent No.: US 6,764,836 B2
(45) Date of Patent: Jul. 20, 2004

(54) INTERLEUKIN-15 RECEPTORS

(75) Inventors: Dirk M. Anderson, Seattle, WA (US); Judith G. Giri, Chesterfield, MO (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 10/385,072

(22) Filed: Mar. 10, 2003

(65) Prior Publication Data

US 2003/0158386 A1 Aug. 21, 2003

Related U.S. Application Data

(63) Continuation of application No. 08/988,197, filed on Dec. 10, 1997, now Pat. No. 6,548,065, which is a continuation of application No. 08/435,760, filed on May 4, 1995, now abandoned, which is a continuation-in-part of application No. 08/300,903, filed on Sep. 6, 1994, now Pat. No. 5,591,630, which is a continuation-in-part of application No. 08/236,919, filed on May 6, 1994, now abandoned.

(51) Int. Cl.[7] .......................... C12P 21/06; C12N 15/00; C07H 21/02; C07H 21/04
(52) U.S. Cl. .................. 435/69.1; 435/320.1; 536/23.1; 536/23.5
(58) Field of Search ............................ 435/69.1, 320.1; 536/23.1, 23.5

(56) References Cited

U.S. PATENT DOCUMENTS

| | | | |
|---|---|---|---|
| 4,925,664 A | 5/1990 | Jackson et al. | |
| 5,194,375 A | 3/1993 | Park et al. | |
| 5,552,303 A | 9/1996 | Grabstein et al. | |
| 5,574,138 A | 11/1996 | Grabstein et al. | |

OTHER PUBLICATIONS

Anderson, D. M. et al., "Functional characterization of the human interleukin–15 receptor α chain and close linkage of IL–15RA and IL–2RA Genes," *J. Bio. Chem.* 270 (50):29862–29869, Dec. 1995, XP002056003.

Burgess et al., "Possible Dissociation of the Heparin–binding and Mitogenic Activities of Heparin–binding (Acidic Fibroblast) Growth Factor–1 from its Receptor–binding Activities by Site–directed Mutagenesis of a Single Lysine Residue," *J. Cell Biol.* 111:2129–2138, 1990.

Carson et al., "Interleukin (IL) 15 is a Novel Cytokine That Activates Human Natural Killer Cells Via Components of the IL–2 Receptor," *J. Exp. Med.* 180:1395–1403, 1994.

Cosman, D. et al., "Interleukin 15 and its receptor," *Ciba Foundation Symposium* 195:221–233, 1995, XP000670929.

Giri et al., "Biochemical Characterization of a Novel Cytokine IL–15 and its Receptor," *J. Cell Biochem.* Supplement, vol. 18D, abstract V561, 1994.

Giri et al., "Utilization of the β and γ chains of the IL–2 receptor by the novel cytokine IL–15," *EMBO J.* 13:2822–2830, 1994.

Giri, J. G. et al., "IL–15, a novel T cell growth factor that shares activities and receptor components with IL–2," *J. Leukocyte Bio.* 57 (5):763–766, May 1995, XP000570466.

Giri, J. G. et al., "Identification and cloning of a novel IL–15 binding protein that is structurally related to the α chain of the IL–2 receptor," *The Embo. Journal* 14(15):3654–3663, 1995, XP002096594.

Grabstein et al., "Cloning of a T Cell Growth Factor That Interacts with the β Chain of the Interleukin–2 Receptor," *Science* 264:965–968, 1994.

Greenberger et al., "Interleukin 3–dependent hematopoietic progenitor cell lines," *Fed. Proc.* 42:2762–2771, 1983.

Kreitman et al., "Mik–β1(Fv)–PE40, A Recombinant Immunotoxin Cytotoxic Toward Cells Bearing the β–Chain of the IL–2 Receptor," *J. Immunol.* 149:2810–2815, 1992.

Kumaki, S. et al., "Subunits of the interleukin 15 receptor," *J. Cell. Biochem. Suppl.* No. 21A:75, Mar. 1995, XP000573660.

Lazar et al., "Transforming Growth Factor α: Mutation of Aspartic Acid 47 and Leucine 48 Results in Different Biological Activities," *Molecular and Cellular Biol.* 8:1247–1252, 1988.

Lindqvist et al., "Expression of Human IL–2 Receptor α– and β–Chains using the Baculovirus Expression System," *Scand. J. Immunol.* 38:267–272, 1993.

Takeshita et al., "Cloning of the γ Chain of the Human IL–2 Receptor," *Science* 257:379–382, 1992.

*Primary Examiner*—Mark Navarro
(74) *Attorney, Agent, or Firm*—Paul B. Tran; Stuart L. Watt; Ron K. Levy

(57) ABSTRACT

There are disclosed Interleukin-15 Receptor (IL-15R) proteins, DNAs and expression vectors encoding IL-15R, and processes for producing IL-15R as products of recombinant cell cultures.

12 Claims, 2 Drawing Sheets

1. ............LLLLLLLRPPAT
          |||||||..  ..|
   MASPQLRGYGVQAIPVLLLLLLLLPLRVT

2. RGITCPPPMSVEHADIWVKSYSLYSRERYICNSGFKRKAGTSSLTECVLNKATNVAHWTTPSLKCIRDP
   .|.|.|.|||:|:||||||:|:.||::.||||:||||||||||.|.|||||.|||||||||||||||
   PGTTCPPPVSIEHADIRVKNYSVNSRERYVCNSGFKRKAGTSTLIECVINKNTNVAHWTTPSLKCIRDP
    --β₁--       --L₁--    --β₂--  --L₂--  --β₃--  ---L₃---  ---β₄---

3. ALVHQRPAPPSTVTTAGVTPQPESLSPSGKEPAASSP
   .|.|.|.| ||.|: ||.|.|||| |||||.|.||
   SLAHYSPVP..TVVTPKVTSQPESPSPSAKEPEAFSP

4. SSNNTAATTAAIVPGSQLMPSKSPSTGTTEISSHESSHGTPSQTTAKTWELTASVSHQPTGVFPQGHSDTT
   .|:.. .|...||||||.| |....|.|||||:.:||.:.||:: || ...:|: ||.|| |:: .|.
   KSDTAMTTETAIMPGSRLTPSQTTSAGTTGTGSHKSSRA.PSLAATMTLEPTASTSLRITEISPHSSKMTK

5. VAISTSTVLLCGLSAVSLLAC
   |||||||||:|::.  .:.:||
   VAISTSVLLVGAGVVMAFLAW

6. YLKSRQTPPLASVEMEAMEALPVTWGTSSRDEDLENCSHHL
   |:|||| .. .|:||.|.|.::| .||.:::.  ...
   YIKSRQPSQPCRVEVETMETVPMTVRASSKEDEDTGA.....

Figure 2

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
       (A) LENGTH: 792 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (ix) FEATURE:
       (A) NAME/KEY: CDS
       (B) LOCATION: 1..789

(xi) SEQUENCE DESCRIPTION: SEQ ID NO: 1:

```
ATG GCC TCG CCG CAG CTC CGG GGC TAT GGA GTC CAG GCC ATT CCT GTG      48
Met Ala Ser Pro Gln Leu Arg Gly Tyr Gly Val Gln Ala Ile Pro Val
 1               5                  10                  15

TTG CTG CTG CTG CTG TTG CTA CTG TTG CTC CCG CTG AGG GTG ACG CCG      96
Leu Leu Leu Leu Leu Leu Leu Leu Leu Leu Pro Leu Arg Val Thr Pro
                20                  25                  30

GGC ACC ACG TGT CCA CCT CCC GTA TCT ATT GAG CAT GCT GAC ATC CGG     144
Gly Thr Thr Cys Pro Pro Pro Val Ser Ile Glu His Ala Asp Ile Arg
                35                  40                  45

GTC AAG AAT TAC AGT GTG AAC TCC AGG GAG AGG TAT GTC TGT AAC TCT     192
Val Lys Asn Tyr Ser Val Asn Ser Arg Glu Arg Tyr Val Cys Asn Ser
         50                  55                  60

GGC TTT AAG CGG AAA GCT GGA ACA TCC ACC CTG ATT GAG TGT GTG ATC     240
Gly Phe Lys Arg Lys Ala Gly Thr Ser Thr Leu Ile Glu Cys Val Ile
 65                  70                  75                  80

AAC AAG AAC ACA AAT GTT GCC CAC TGG ACA ACT CCC AGC CTC AAG TGC     288
Asn Lys Asn Thr Asn Val Ala His Trp Thr Thr Pro Ser Leu Lys Cys
                85                  90                  95

ATC AGA GAC CCC TCC CTA GCT CAC TAC AGT CCA GTG CCA ACA GTA GTG     336
Ile Arg Asp Pro Ser Leu Ala His Tyr Ser Pro Val Pro Thr Val Val
                100                 105                 110

ACA CCA AAG GTG ACC TCA CAG CCA GAG AGC CCC TCC CCC TCT GCA AAA     384
Thr Pro Lys Val Thr Ser Gln Pro Glu Ser Pro Ser Pro Ser Ala Lys
                115                 120                 125

GAG CCA GAA GCT TTC TCT CCC AAA TCA GAT ACC GCA ATG ACC ACA GAG     432
Glu Pro Glu Ala Phe Ser Pro Lys Ser Asp Thr Ala Met Thr Thr Glu
        130                 135                 140

ACA GCT ATT ATG CCT GGC TCC AGG CTG ACA CCA TCC CAA ACA ACT TCT     480
Thr Ala Ile Met Pro Gly Ser Arg Leu Thr Pro Ser Gln Thr Thr Ser
145                 150                 155                 160

GCA GGA ACT ACA GGG ACA GGC AGT CAC AAG TCC TCC CGA GCC CCA TCT     528
Ala Gly Thr Thr Gly Thr Gly Ser His Lys Ser Ser Arg Ala Pro Ser
                165                 170                 175

CTT GCA GCA ACA ATG ACC TTG GAG CCT ACA GCC TCC ACC TCC CTC AGG     576
Leu Ala Ala Thr Met Thr Leu Glu Pro Thr Ala Ser Thr Ser Leu Arg
                180                 185                 190

ATA ACA GAG ATT TCT CCC CAC AGT TCC AAA ATG ACG AAA GTG GCC ATC     624
Ile Thr Glu Ile Ser Pro His Ser Ser Lys Met Thr Lys Val Ala Ile
                195                 200                 205
```

```
TCT ACA TCG GTC CTC TTG GTT GGT GCA GGG GTT GTG ATG GCT TTC CTG    672
Ser Thr Ser Val Leu Leu Val Gly Ala Gly Val Val Met Ala Phe Leu
    210                 215                 220

GCC TGG TAC ATC AAA TCA AGG CAG CCT TCT CAG CCG TGC CGT GTT GAG    720
Ala Trp Tyr Ile Lys Ser Arg Gln Pro Ser Gln Pro Cys Arg Val Glu
225                 230                 235                 240

GTG GAA ACC ATG GAA ACA GTA CCA ATG ACT GTG AGG GCC AGC AGC AAG    768
Val Glu Thr Met Glu Thr Val Pro Met Thr Val Arg Ala Ser Ser Lys
                245                 250                 255

GAG GAT GAA GAC ACA GGA GCC TAA                                    792
Glu Asp Glu Asp Thr Gly Ala
            260
```

(2) INFORMATION FOR SEQ ID NO: 2:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ser Pro Gln Leu Arg Gly Tyr Gly Val Gln Ala Ile Pro Val
1               5                   10                  15

Leu Leu Leu Leu Leu Leu Leu Leu Leu Pro Leu Arg Val Thr Pro
                20                  25                  30

Gly Thr Thr Cys Pro Pro Pro Val Ser Ile Glu His Ala Asp Ile Arg
                35                  40                  45

Val Lys Asn Tyr Ser Val Asn Ser Arg Glu Arg Tyr Val Cys Asn Ser
            50                  55                  60

Gly Phe Lys Arg Lys Ala Gly Thr Ser Thr Leu Ile Glu Cys Val Ile
65                  70                  75                  80

Asn Lys Asn Thr Asn Val Ala His Trp Thr Thr Pro Ser Leu Lys Cys
                85                  90                  95

Ile Arg Asp Pro Ser Leu Ala His Tyr Ser Pro Val Pro Thr Val Val
                100                 105                 110

Thr Pro Lys Val Thr Ser Gln Pro Glu Ser Pro Ser Pro Ser Ala Lys
            115                 120                 125

Glu Pro Glu Ala Phe Ser Pro Lys Ser Asp Thr Ala Met Thr Thr Glu
130                 135                 140

Thr Ala Ile Met Pro Gly Ser Arg Leu Thr Pro Ser Gln Thr Thr Ser
145                 150                 155                 160

Ala Gly Thr Thr Gly Thr Gly Ser His Lys Ser Ser Arg Ala Pro Ser
                165                 170                 175

Leu Ala Ala Thr Met Thr Leu Glu Pro Thr Ala Ser Thr Ser Leu Arg
                180                 185                 190

Ile Thr Glu Ile Ser Pro His Ser Ser Lys Met Thr Lys Val Ala Ile
            195                 200                 205

Ser Thr Ser Val Leu Leu Val Gly Ala Gly Val Val Met Ala Phe Leu
            210                 215                 220

Ala Trp Tyr Ile Lys Ser Arg Gln Pro Ser Gln Pro Cys Arg Val Glu
225                 230                 235                 240

Val Glu Thr Met Glu Thr Val Pro Met Thr Val Arg Ala Ser Ser Lys
                245                 250                 255

Glu Asp Glu Asp Thr Gly Ala
            260
```

(2) INFORMATION FOR SEQ ID NO: 3:

(i) SEQUENCE CHARACTERISTICS:
        (A) LENGTH: 122 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO: 3:

```
Asp Tyr Lys Asp Asp Asp Asp Lys Asn Trp Val Asn Val Ile Ser Asp
 1               5                  10                  15

Leu Lys Lys Ile Glu Asp Leu Ile Gln Ser Met His Ile Asp Ala Thr
            20                  25                  30

Leu Tyr Thr Glu Ser Asp Val His Pro Ser Cys Lys Val Thr Ala Met
        35                  40                  45

Lys Cys Phe Leu Leu Glu Leu Gln Val Ile Ser His Glu Ser Gly Asp
    50                  55                  60

Thr Asp Ile His Asp Thr Val Glu Asn Leu Ile Ile Leu Ala Asn Asn
65                  70                  75                  80

Ile Leu Ser Ser Asn Gly Asn Ile Thr Glu Ser Gly Cys Lys Glu Cys
                85                  90                  95

Glu Glu Leu Glu Glu Lys Asn Ile Lys Glu Phe Leu Gln Ser Phe Val
            100                 105                 110

His Ile Val Gln Met Phe Ile Asn Thr Ser
        115                 120
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

GATCTTGGAA CGAGACGACC TGCT                                      24

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

AGCAGGTCGT CTCGTTCCAA                                          20

(2) INFORMATION FOR SEQ ID NO: 6:

```
    (i) SEQUENCE CHARACTERISTICS:
        (A) LENGTH: 1534 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..753

(xi) SEQUENCE DESCRIPTION: SEQ ID NO: 6:

CTG CTA CTG CTG CTG CTG CTC CGG CCG CCG GCG ACG CGG GGC ATC ACG        48
Leu Leu Leu Leu Leu Leu Leu Arg Pro Pro Ala Thr Arg Gly Ile Thr
 1               5                  10                  15

TGC CCT CCC CCC ATG TCC GTG GAA CAC GCA GAC ATC TGG GTC AAG AGC        96
Cys Pro Pro Pro Met Ser Val Glu His Ala Asp Ile Trp Val Lys Ser
                20                  25                  30

TAC AGC TTG TAC TCC AGG GAG CGG TAC ATT TGT AAC TCT GGT TTC AAG       144
Tyr Ser Leu Tyr Ser Arg Glu Arg Tyr Ile Cys Asn Ser Gly Phe Lys
            35                  40                  45

CGT AAA GCC GGC ACG TCC AGC CTG ACG GAG TGC GTG TTG AAC AAG GCC       192
Arg Lys Ala Gly Thr Ser Ser Leu Thr Glu Cys Val Leu Asn Lys Ala
 50                  55                  60

ACG AAT GTC GCC CAC TGG ACA ACC CCC AGT CTC AAA TGC ATT AGA GAC       240
Thr Asn Val Ala His Trp Thr Thr Pro Ser Leu Lys Cys Ile Arg Asp
 65                  70                  75                  80

CCT GCC CTG GTT CAC CAA AGG CCA GCG CCA CCC TCC ACA GTA ACG ACG       288
Pro Ala Leu Val His Gln Arg Pro Ala Pro Pro Ser Thr Val Thr Thr
                 85                  90                  95

GCA GGG GTG ACC CCA CAG CCA GAG AGC CTC TCC CCT TCT GGA AAA GAG       336
Ala Gly Val Thr Pro Gln Pro Glu Ser Leu Ser Pro Ser Gly Lys Glu
                100                 105                 110

CCC GCA GCT TCA TCT CCC AGC TCA AAC AAC ACA GCG GCC ACA ACA GCA       384
Pro Ala Ala Ser Ser Pro Ser Ser Asn Asn Thr Ala Ala Thr Thr Ala
            115                 120                 125

GCT ATT GTC CCG GGC TCC CAG CTG ATG CCT TCA AAA TCA CCT TCC ACA       432
Ala Ile Val Pro Gly Ser Gln Leu Met Pro Ser Lys Ser Pro Ser Thr
130                 135                 140

GGA ACC ACA GAG ATA AGC AGT CAT GAG TCC TCC CAC GGC ACC CCC TCT       480
Gly Thr Thr Glu Ile Ser Ser His Glu Ser Ser His Gly Thr Pro Ser
145                 150                 155                 160

CAG ACA ACA GCC AAG ACC TGG GAA CTC ACA GCA TCC GCC TCC CAC CAG       528
Gln Thr Thr Ala Lys Thr Trp Glu Leu Thr Ala Ser Ala Ser His Gln
                165                 170                 175

CCG CCA GGT GTG TAT CCA CAG GGC CAC AGC GAC ACC ACT GTG GCT ATC       576
Pro Pro Gly Val Tyr Pro Gln Gly His Ser Asp Thr Thr Val Ala Ile
            180                 185                 190

TCC ACG TCC ACT GTC CTG CTG TGT GGG CTG AGC GCT GTG TCT CTC CTG       624
Ser Thr Ser Thr Val Leu Leu Cys Gly Leu Ser Ala Val Ser Leu Leu
            195                 200                 205

GCA TGC TAC CTC AAG TCA AGG CAA ACT CCC CCG CTG GCC AGC GTT GAA       672
Ala Cys Tyr Leu Lys Ser Arg Gln Thr Pro Pro Leu Ala Ser Val Glu
210                 215                 220

ATG GAA GCC ATG GAG GCT CTG CCG GTG ACT TGG GGG ACC AGC AGC AGA       720
Met Glu Ala Met Glu Ala Leu Pro Val Thr Trp Gly Thr Ser Ser Arg
225                 230                 235                 240
```

-continued

```
GAT GAA GAC TTG GAA AAC TGC TCT CAC CAC CTA TGAAACTCGG GGAAACCAGC    773
Asp Glu Asp Leu Glu Asn Cys Ser His His Leu
            245                 250

CCAGCTAAGT CCGGAGTGAA GGAGCCTCTC TGCTTTAGCT AAAGACGACT GAGAAGAGGT    833

GCAAGGAAGC GGGCTCCAGG AGCAAGCTCA CCAGGCCTCT CAGAAGTCCC AGCAGGATCT    893

CACGGACTGC CGGGTCGGCG CCTCCTGCGC GAGGGAGCAG GTTCTCCGCA TTCCCATGGG    953

CACCACCTGC CTGCCTGTCG TGCCTTGGAC CCAGGGCCCA GCTTCCCAGG AGAGACCAAA   1013

GGCTTCTGAG CAGGATTTTT ATTTCATTAC AGTGTGAGCT GCCTGGAATA CATGTGGTAA   1073

TGAAATAAAA ACCCTGCCCC GAATCTTCCG TCCCTCATCC TAACTTGCAG TTCACAGAGA   1133

AAAGTGACAT ACCCAAAGCT CTCTGTCAAT TACAAGGCTT CTCCTGGCGT GGGAGACGTC   1193

TACAGGGAAG ACACCAGCGT TTGGGCTTCT AACCACCCTG TCTCCAGCTG CTCTGCACAC   1253

ATGGACAGGG ACCTGGGAAA GGTGGGAGAG ATGCTGAGCC CAGCGAATCC TCTCCATTGA   1313

AGGATTCAGG AAGAAGAAAA CTCAACTCAG TGCCATTTTA CGAATATATG CGTTTATATT   1373

TATACTTCCT TGTCTATTAT ATCTATACAT TATATATTAT TTGTATTTTG ACATTGTACC   1433

TTGTATAAAC AAAATAAAAC ATCTATTTTC AATATTTTTA AAATGCAAAA AAAAAAAAA    1493

AAAAAAAAAA AAAAAAAAAA AAAAAAAAAA AAAAAAAAA A                        1534
```

(2) INFORMATION FOR SEQ ID NO: 7:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO: 7:

```
Leu Leu Leu Leu Leu Leu Leu Arg Pro Pro Ala Thr Arg Gly Ile Thr
 1               5                  10                  15

Cys Pro Pro Pro Met Ser Val Glu His Ala Asp Ile Trp Val Lys Ser
                20                  25                  30

Tyr Ser Leu Tyr Ser Arg Glu Arg Tyr Ile Cys Asn Ser Gly Phe Lys
            35                  40                  45

Arg Lys Ala Gly Thr Ser Ser Leu Thr Glu Cys Val Leu Asn Lys Ala
        50                  55                  60

Thr Asn Val Ala His Trp Thr Thr Pro Ser Leu Lys Cys Ile Arg Asp
65                  70                  75                  80

Pro Ala Leu Val His Gln Arg Pro Ala Pro Pro Ser Thr Val Thr Thr
                85                  90                  95

Ala Gly Val Thr Pro Gln Pro Glu Ser Leu Ser Pro Ser Gly Lys Glu
            100                 105                 110

Pro Ala Ala Ser Ser Pro Ser Ser Asn Asn Thr Ala Ala Thr Thr Ala
        115                 120                 125

Ala Ile Val Pro Gly Ser Gln Leu Met Pro Ser Lys Ser Pro Ser Thr
    130                 135                 140

Gly Thr Thr Glu Ile Ser Ser His Glu Ser Ser His Gly Thr Pro Ser
145                 150                 155                 160

Gln Thr Thr Ala Lys Thr Trp Glu Leu Thr Ala Ser Ala Ser His Gln
                165                 170                 175

Pro Pro Gly Val Tyr Pro Gln Gly His Ser Asp Thr Thr Val Ala Ile
            180                 185                 190

Ser Thr Ser Thr Val Leu Leu Cys Gly Leu Ser Ala Val Ser Leu Leu
```

```
               195                 200                     205
    Ala Cys Tyr Leu Lys Ser Arg Gln Thr Pro Leu Ala Ser Val Glu
        210                 215                 220

Met Glu Ala Met Glu Ala Leu Pro Val Thr Trp Gly Thr Ser Ser Arg
    225                 230                 235                 240

Asp Glu Asp Leu Glu Asn Cys Ser His His Leu
                    245                 250

(2) INFORMATION FOR SEQ ID NO: 8:

(i) SEQUENCE CHARACTERISTICS:
        (A) LENGTH: 1641 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 3..839

(xi) SEQUENCE DESCRIPTION: SEQ ID NO: 8:

CG CGC GGC TGC CGG ACC CTC GGT CTC CCG GCG CTG CTA CTG CTG CTG          47
   Arg Gly Cys Arg Thr Leu Gly Leu Pro Ala Leu Leu Leu Leu Leu
    1               5                  10                  15

CTG CTC CGG CCG CCG GCG ACG CGG GAT GCA AGA GAC AGG CTG GCT GTC         95
Leu Leu Arg Pro Pro Ala Thr Arg Asp Ala Arg Asp Arg Leu Ala Val
                20                  25                  30

CTG GCG GGA AGG AGC AGA ATA TCT GAA AGC TTC AAC CAT GAG GTC CAG         143
Leu Ala Gly Arg Ser Arg Ile Ser Glu Ser Phe Asn His Glu Val Gln
            35                  40                  45

ACA CAC GAG GCC TGC GTG AGA CTC AGG ACA ATG GAA AAC TGC CCC CAG         191
Thr His Glu Ala Cys Val Arg Leu Arg Thr Met Glu Asn Cys Pro Gln
        50                  55                  60

TGC CAC CAC CAT CGG ACA AGC AGG CAG CAA GCA GGC ATC ACG TGC CCT         239
Cys His His His Arg Thr Ser Arg Gln Gln Ala Gly Ile Thr Cys Pro
    65                  70                  75

CCC CCC ATG TCC GTG GAA CAC GCA GAC ATC TGG GTC AAG AGC TAC AGC         287
Pro Pro Met Ser Val Glu His Ala Asp Ile Trp Val Lys Ser Tyr Ser
80                  85                  90                  95

TTG TAC TCC AGG GAG CGG TAC ATT TGT AAC TCT GGT TTC AAG CGT AAA         335
Leu Tyr Ser Arg Glu Arg Tyr Ile Cys Asn Ser Gly Phe Lys Arg Lys
                100                 105                 110

GCC GGC ACG TCC AGC CTG ACG GAG TGC GTG TTG AAC AAG GCC ACG AAT         383
Ala Gly Thr Ser Ser Leu Thr Glu Cys Val Leu Asn Lys Ala Thr Asn
            115                 120                 125

GTC GCC CAC TGG ACA ACC CCC AGT CTC AAA TGC ATT AAG CCC GCA GCT         431
Val Ala His Trp Thr Thr Pro Ser Leu Lys Cys Ile Lys Pro Ala Ala
        130                 135                 140

TCA TCT CCC AGC TCA AAC AAC ACA GCG GCC ACA ACA GCA GCT ATT GTC         479
Ser Ser Pro Ser Ser Asn Asn Thr Ala Ala Thr Thr Ala Ala Ile Val
    145                 150                 155

CCG GGC TCC CAG CTG ATG CCT TCA AAA TCA CCT TCC ACA GGA ACC ACA         527
Pro Gly Ser Gln Leu Met Pro Ser Lys Ser Pro Ser Thr Gly Thr Thr
160                 165                 170                 175

GAG ATA AGC AGT CAT GAG TCC TCC CAC GGC ACC CCC TCT CAG ACA ACA         575
Glu Ile Ser Ser His Glu Ser Ser His Gly Thr Pro Ser Gln Thr Thr
                180                 185                 190
```

```
GCC AAG ACC TGG GAA CTC ACA GCA TCC GCC TCC CAC CAG CCG CCA GGT      623
Ala Lys Thr Trp Glu Leu Thr Ala Ser Ala Ser His Gln Pro Pro Gly
            195                 200                 205

GTG TAT CCA CAG GGC CAC AGC GAC ACC ACT GTG GCT ATC TCC ACG TCC      671
Val Tyr Pro Gln Gly His Ser Asp Thr Thr Val Ala Ile Ser Thr Ser
                210                 215                 220

ACT GTC CTG CTG TGT GGG CTG AGC GCT GTG TCT CTC CTG GCA TGC TAC      719
Thr Val Leu Leu Cys Gly Leu Ser Ala Val Ser Leu Leu Ala Cys Tyr
            225                 230                 235

CTC AAG TCA AGG CAA ACT CCC CCG CTG GCC AGC GTT GAA ATG GAA GCC      767
Leu Lys Ser Arg Gln Thr Pro Pro Leu Ala Ser Val Glu Met Glu Ala
240                 245                 250                 255

ATG GAG GCT CTG CCG GTG ACT TGG GGG ACC AGC AGC AGA GAT GAA GAC      815
Met Glu Ala Leu Pro Val Thr Trp Gly Thr Ser Ser Arg Asp Glu Asp
                260                 265                 270

TTG GAA AAC TGC TCT CAC CAC CTA TGAAACTCAG GGAAACCAGC CCAGCTAAGT     869
Leu Glu Asn Cys Ser His His Leu
                275

CCGGAGTGAA GGAGCCTCTC TGCTTTAGCT AAAGACGACT GAGAAGAGGT GCAAGGAAGC    929

GGGCTCCAGG AGCAAGCTCA CCAGGCCTCT CAGAAGTCCC AGCAGGATCT CACGGACTGC    989

CGGGTCGGCG CCTCCTGCGC GAGGGAGCAG GTTCTCCGCA TTCCCATGGG CACCACCTGC   1049

CTGCCTGTCG TGCCTTGGAC CCAGGGCCCA GCTTCCCAGG AGAGACCAAA GGCTTCTGAG   1109

CAGGATTTTT ATTTCATTAC AGTGTGAGCT GCCTGGAATA CATGTGGTAA TGAAATAAAA   1169

ACCCTGCCCC GAATCTTCCG TCCCTCATCC TAACTTGCAG TTCACAGAGA AAAGTGACAT   1229

ACCCAAAGCT CTCTGTCAAT TACAAGGCTT CTCCTGGCGT GGGAGACGTC TACAGGGAAG   1289

ACACCAGCGT TTGGGCTTCT AACCACCCTG TCTCCAGCTG CTCTGCACAC ATGGACAGGG   1349

ACCTGGGAAA GGTGGGAGAG ATGCTGAGCC CAGCGAATCC TCTCCATTGA AGGATTCAGG   1409

AAGAAGAAAA CTCAACTCAG TGCCATTTTA CGAATATATG CGTTTATATT TATACTTCCT   1469

TGTCTATTAT ATCTATACAT TATATATTAT TTGTATTTTG ACATTGTACC TTGTATAAAC   1529

AAAATAAAAC ATCTATTTTC AATAAAAAAA AAAAAAAAAA AAAAAAAAAA AAAAAAAAAA   1589

AAAAAAAAAA AAAAAAAAAA AAAAAAAAAA AAAAAAAAA AAAAAAAAAA AA           1641

(2) INFORMATION FOR SEQ ID NO: 9:

(i) SEQUENCE CHARACTERISTICS:
        (A) LENGTH: 279 amino acids
        (B) TYPE: amino acid
        (D) TOPOLOGY: linear (ii) MOLECULE TYPE: protein (xi) SEQUENCE DESCRIPTION: SEQ ID NO: 9:

Arg Gly Cys Arg Thr Leu Gly Leu Pro Ala Leu Leu Leu Leu Leu Leu
1               5                   10                  15

Leu Arg Pro Pro Ala Thr Arg Asp Ala Arg Asp Arg Leu Ala Val Leu
                20                  25                  30

Ala Gly Arg Ser Arg Ile Ser Glu Ser Phe Asn His Glu Val Gln Thr
            35                  40                  45

His Glu Ala Cys Val Arg Leu Arg Thr Met Glu Asn Cys Pro Gln Cys
        50                  55                  60

His His His Arg Thr Ser Arg Gln Gln Ala Gly Ile Thr Cys Pro Pro
65                  70                  75                  80

Pro Met Ser Val Glu His Ala Asp Ile Trp Val Lys Ser Tyr Ser Leu
```

```
                 85                  90                  95
Tyr Ser Arg Glu Arg Tyr Ile Cys Asn Ser Gly Phe Lys Arg Lys Ala
                100                 105                 110

Gly Thr Ser Ser Leu Thr Glu Cys Val Leu Asn Lys Ala Thr Asn Val
            115                 120                 125

Ala His Trp Thr Thr Pro Ser Leu Lys Cys Ile Lys Pro Ala Ala Ser
        130                 135                 140

Ser Pro Ser Ser Asn Asn Thr Ala Ala Thr Ala Ala Ile Val Pro
145                 150                 155                 160

Gly Ser Gln Leu Met Pro Ser Lys Ser Pro Ser Thr Gly Thr Thr Glu
                165                 170                 175

Ile Ser Ser His Glu Ser Ser His Gly Thr Pro Ser Gln Thr Thr Ala
                180                 185                 190

Lys Thr Trp Glu Leu Thr Ala Ser Ala Ser His Gln Pro Pro Gly Val
                195                 200                 205

Tyr Pro Gln Gly His Ser Asp Thr Thr Val Ala Ile Ser Thr Ser Thr
    210                 215                 220

Val Leu Leu Cys Gly Leu Ser Ala Val Ser Leu Leu Ala Cys Tyr Leu
225                 230                 235                 240

Lys Ser Arg Gln Thr Pro Pro Leu Ala Ser Val Glu Met Glu Ala Met
                245                 250                 255

Glu Ala Leu Pro Val Thr Trp Gly Thr Ser Ser Arg Asp Glu Asp Leu
                260                 265                 270

Glu Asn Cys Ser His His Leu
            275

(2) INFORMATION FOR SEQ ID NO: 10:

(i) SEQUENCE CHARACTERISTICS:
        (A) LENGTH: 1474 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 83..784

(xi) SEQUENCE DESCRIPTION: SEQ ID NO: 10:

CCCAGAGCAG CGCTCGCCAC CTCCCCCCGG CCTGGGCAGC GCTCGCCCGG GGAGTCCAGC        60

GGTGTCCTGT GGAGCTGCCG CC ATG GCC CCG CGG CGG GCG CGC GGC TGC CGG       112
                         Met Ala Pro Arg Arg Ala Arg Gly Cys Arg
                          1               5                  10

ACC CTC GGT CTC CCG GCG CTG CTA CTG CTG CTG CTG CTC CGG CCG CCG        160
Thr Leu Gly Leu Pro Ala Leu Leu Leu Leu Leu Leu Leu Arg Pro Pro
            15                  20                  25

GCG ACG CGG GGC ATC ACG TGC CCT CCC CCC ATG TCC GTG GAA CAC GCA        208
Ala Thr Arg Gly Ile Thr Cys Pro Pro Pro Met Ser Val Glu His Ala
        30                  35                  40

GAC ATC TGG GTC AAG AGC TAC AGC TTG TAC TCC AGG GAG CGG TAC ATT        256
Asp Ile Trp Val Lys Ser Tyr Ser Leu Tyr Ser Arg Glu Arg Tyr Ile
    45                  50                  55

TGT AAC TCT GGT TTC AAG CGT AAA GCC GGC ACG TCC AGC CTG ACG GAG        304
Cys Asn Ser Gly Phe Lys Arg Lys Ala Gly Thr Ser Ser Leu Thr Glu
```

```
      60              65              70
TGC GTG TTG AAC AAG GCC ACG AAT GTC GCC CAC TGG ACA ACC CCC AGT    352
Cys Val Leu Asn Lys Ala Thr Asn Val Ala His Trp Thr Thr Pro Ser
 75              80              85              90

CTC AAA TGC ATT AAG CCC GCA GCT TCA TCT CCC AGC TCA AAC AAC ACA    400
Leu Lys Cys Ile Lys Pro Ala Ala Ser Ser Pro Ser Ser Asn Asn Thr
                 95              100             105

GCG GCC ACA ACA GCA GCT ATT GTC CCG GGC TCC CAG CTG ATG CCT TCA    448
Ala Ala Thr Thr Ala Ala Ile Val Pro Gly Ser Gln Leu Met Pro Ser
             110             115             120

AAA TCA CCT TCC ACA GGA ACC ACA GAG ATA AGC AGT CAT GAG TCC TCC    496
Lys Ser Pro Ser Thr Gly Thr Thr Glu Ile Ser Ser His Glu Ser Ser
         125             130             135

CAC GGC ACC CCC TCT CAG ACA ACA GCC AAG AAC TGG GAA CTC ACA GCA    544
His Gly Thr Pro Ser Gln Thr Thr Ala Lys Asn Trp Glu Leu Thr Ala
     140             145             150

TCC GCC TCC CAC CAG CCG CCA GGT GTG TAT CCA CAG GGC CAC AGC GAC    592
Ser Ala Ser His Gln Pro Pro Gly Val Tyr Pro Gln Gly His Ser Asp
155             160             165             170

ACC ACT GTG GCT ATC TCC ACG TCC ACT GTC CTG CTG TGT GGG CTG AGC    640
Thr Thr Val Ala Ile Ser Thr Ser Thr Val Leu Leu Cys Gly Leu Ser
             175             180             185

GCT GTG TCT CTC CTG GCA TGC TAC CTC AAG TCA AGG CAA ACT CCC CCG    688
Ala Val Ser Leu Leu Ala Cys Tyr Leu Lys Ser Arg Gln Thr Pro Pro
         190             195             200

CTG GCC AGC GTT GAA ATG GAA GCC ATG GAG GCT CTG CCG GTG ACT TGG    736
Leu Ala Ser Val Glu Met Glu Ala Met Glu Ala Leu Pro Val Thr Trp
     205             210             215

GGG ACC AGC AGC AGA GAT GAA GAC TTG GAA AAC TGC TCT CAC CAC CTA    784
Gly Thr Ser Ser Arg Asp Glu Asp Leu Glu Asn Cys Ser His His Leu
220             225             230

TGAAACTCGG GGAAACCAGC CCAGCTAAGT CCGGAGTGAA GGAGCCTCTC TGCTTTAGCT    844
AAAGACGACT GAGAAGAGGT GCAAGGAAGC GGGCTCCAGG AGCAAGCTCA CCAGGCCTCT    904
CAGAAGTCCC AGCAGGATCT CACGGACTGC CGGGTCGGCG CCTCCTGCGC GAGGGAGCAG    964
GTTCTCCGCA TTCCCATGGG CACCACCTGC CTGCCTGTCG TGCCTTGGAC CCAGGGCCCA   1024
GCTTCCCAGG AGAGACCAAA GGCTTCTGAG CAGGATTTTT ATTTCATTAC AGTGTGAGCT   1084
GCCTGGAATA CATGTGGTAA TGAAATAAAA ACCCTGCCCC GAATCTTCCG TCCCTCATCC   1144
TAACTTTCAG TTCACAGAGA AAAGTGACAT ACCCAAAGCT CTCTGTCAAT TACAAGGCTT   1204
CTCCTGGCGT GGGAGACGTC TACAGGGAAG ACACCAGCGT TTGGGCTTCT AACCACCCTG   1264
TCTCCAGCTG CTCTGCACAC ATGGACAGGG ACCTGGGAAA GGTGGGAGAG ATGCTGAGCC   1324
CAGCGAATCC TCTCCATTGA AGGATTCAGG AAGAAGAAAA CTCAACTCAG TGCCATTTTA   1384
CGAATATATG CGTTTATATT TATACTTCCT TGTCTATTAT ATCTATACAT TATATATTAT   1444
TTGTATTTTG ACATTGTACC TTGTATAAAC                                   1474

(2) INFORMATION FOR SEQ ID NO: 11:

(i) SEQUENCE CHARACTERISTICS:
        (A) LENGTH: 234 amino acids
        (B) TYPE: amino acid
        (D) TOPOLOGY: linear (ii) MOLECULE TYPE: protein (xi) SEQUENCE DESCRIPTION: SEQ ID NO: 11:

Met Ala Pro Arg Arg Ala Arg Gly Cys Arg Thr Leu Gly Leu Pro Ala
```

```
          1               5              10              15
Leu Leu Leu Leu Leu Leu Leu Arg Pro Pro Ala Thr Arg Gly Ile Thr
              20                  25                  30

Cys Pro Pro Pro Met Ser Val Glu His Ala Asp Ile Trp Val Lys Ser
              35                  40                  45

Tyr Ser Leu Tyr Ser Arg Glu Arg Tyr Ile Cys Asn Ser Gly Phe Lys
              50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Lys Pro
                 85                  90                  95

Ala Ala Ser Ser Pro Ser Ser Asn Asn Thr Ala Ala Thr Thr Ala Ala
             100                 105                 110

Ile Val Pro Gly Ser Gln Leu Met Pro Ser Lys Ser Pro Ser Thr Gly
             115                 120                 125

Thr Thr Glu Ile Ser Ser His Glu Ser Ser His Gly Thr Pro Ser Gln
             130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr Val Ala Ile Ser
                 165                 170                 175

Thr Ser Thr Val Leu Leu Cys Gly Leu Ser Ala Val Ser Leu Leu Ala
             180                 185                 190

Cys Tyr Leu Lys Ser Arg Gln Thr Pro Pro Leu Ala Ser Val Glu Met
             195                 200                 205

Glu Ala Met Glu Ala Leu Pro Val Thr Trp Gly Thr Ser Ser Arg Asp
210                 215                 220

Glu Asp Leu Glu Asn Cys Ser His His Leu
225                 230

(2) INFORMATION FOR SEQ ID NO: 12:

(i) SEQUENCE CHARACTERISTICS:
        (A) LENGTH: 1510 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 3..356

(xi) SEQUENCE DESCRIPTION: SEQ ID NO: 12:

CC AGC TCA AAC AAC ACA GCG GCC ACA ACA GCA GCT ATT GTC CCG GGC        47
   Ser Ser Asn Asn Thr Ala Ala Thr Thr Ala Ala Ile Val Pro Gly
    1               5                  10                  15

TCC CAG CTG ATG CCT TCA AAA TCA CCT TCC ACA GGA ACC ACA GAG ATA       95
Ser Gln Leu Met Pro Ser Lys Ser Pro Ser Thr Gly Thr Thr Glu Ile
             20                  25                  30

AGC AGT CAT GAG TCC TCC CAC GGC ACC CCC TCT CAG ACA ACA GCC AAG      143
Ser Ser His Glu Ser Ser His Gly Thr Pro Ser Gln Thr Thr Ala Lys
             35                  40                  45

AAC TGG GAA CTC ACA GCA TCC GCC TCC CAC CAG CCG CCA GGT GTG TAT      191
Asn Trp Glu Leu Thr Ala Ser Ala Ser His Gln Pro Pro Gly Val Tyr
```

-continued

```
              50                  55                  60
CCA CAG GGC CAC AGC GAC ACC ACT GTG GCT ATC TCC ACG TCC ACT GTC       239
Pro Gln Gly His Ser Asp Thr Thr Val Ala Ile Ser Thr Ser Thr Val
         65                  70                  75

CTG CTG TGT GGG CTG AGC GCT GTG TCT CTC CTG GCA TGC TAC CTC AAG       287
Leu Leu Cys Gly Leu Ser Ala Val Ser Leu Leu Ala Cys Tyr Leu Lys
 80                  85                  90                  95

TCA AGG GCC TCT GTC TGC TCC TGC CAT CCC CGC AGT GCT GGA CAT ACA       335
Ser Arg Ala Ser Val Cys Ser Cys His Pro Arg Ser Ala Gly His Thr
                    100                 105                 110

TGC TCA GTG GGA AGC GTC TGT TGATTTGAGG GCAACCCCCT CCTCTTTTCA          386
Cys Ser Val Gly Ser Val Cys
                115

AAACCTATGA ACCACCTGCT TTGCAGGCAA ACTCCCCCGC TGGCCAGCGT TGAAATGGAA     446
GCCATGGAGG CTCTGCCGGT GACTTGGGGG ACCAGCAGCA GAGATGAAGA CTTGGAAAAC     506
TGCTCTCACC ACCTATGAAA CTCGGGGAAA CCAGCCCAGC TAAGTCCGGA GTGAAGGAGC     566
CTCTCTGCTT TAGCTAAAGA CGACTGAGAA GAGGTGCAAG GAAGCGGGCT CCAGGAGCAA     626
GCTCACCAGG CCTCTCAGAA GTCCCAGCAG GATCTCACGG ACTGCCGGGT CGGCGCCTCC     686
TGCGCGAGGG AGCAGGTTCT CCGCATTCCC ATGGGCACCA CCTGCCTGCC TGTCGTGCCT     746
TGGACCCAGG GCCCAGCTTC CCAGGAGAGA CCAAAGGCTT CTGAGCAGGA TTTTTATTTC     806
ATTACAGTGT GAGCTGCCTG GAATACATGT GGTAATGAAA TAAAAACCCT GCCCCGAATC     866
TTCCGTCCCT CATCCTAACT TTCAGTTCAC AGAGAAAAGT GACATACCCA AAGCTCTCTG     926
TCAATTACAA GGCTTCTCCT GGCCTGGGAG ACGTCTACAG GGAAGACACC AGCGTTTGGG     986
CTTCTAACCA CCCTGTCTCC AGCTGCTCTG CACACATGGA CAGGGACCTG GGAAAGGTGG    1046
GAGAGATGCT GAGCCCAGCG AATCCTCTCC ATTGAAGGAT TCAGGAAGAA GAAAACTCAA    1106
CTCAGTGCCA TTTACGAAT ATATGCGTTT ATATTTATAC TTCCTTGTCT ATTATATCTA     1166
TACATTATAT ATTATTTGTA TTTTGACATT GTACCTTGTA TAAACAAAAT AAAACATCTA    1226
TTTTCAATAT TTTTAAAATG CATTAAGAGA ATCACCAAGG AGAAATGTTC CACATAAAGG    1286
AGGAGAAAGA GTAGGAAGGC AGAGTCCAAG GTGACTGAGT TCAGGTGTTC TTTCCAGAAG    1346
GAGAAAAAGC CTTGCCTAAA GCTGGCTCCG GTCACAGTTT TGGGGAATTT CCCACAATTC    1406
CATGTGAGGA GAAGCAGCAT TATCTAATCC ACACAGTGGC AAGTCTGGGC TCAGCTCCCC    1466
AGTGGTATAC ACATCGTCTC TTCCCTTCTT CTTCTCTTAC TTTC                    1510
```

(2) INFORMATION FOR SEQ ID NO: 13:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 13:

```
Ser Ser Asn Asn Thr Ala Ala Thr Thr Ala Ala Ile Val Pro Gly Ser
 1               5                  10                  15

Gln Leu Met Pro Ser Lys Ser Pro Ser Thr Gly Thr Thr Glu Ile Ser
                20                  25                  30

Ser His Glu Ser Ser His Gly Thr Pro Ser Gln Thr Thr Ala Lys Asn
            35                  40                  45

Trp Glu Leu Thr Ala Ser Ala Ser His Gln Pro Pro Gly Val Tyr Pro
 50                  55                  60
```

```
Gln Gly His Ser Asp Thr Thr Val Ala Ile Ser Thr Ser Thr Val Leu
 65                  70                  75                  80

Leu Cys Gly Leu Ser Ala Val Ser Leu Leu Ala Cys Tyr Leu Lys Ser
                 85                  90                  95

Arg Ala Ser Val Cys Ser Cys His Pro Arg Ser Ala Gly His Thr Cys
                100                 105                 110

Ser Val Gly Ser Val Cys
        115
```

(2) INFORMATION FOR SEQ ID NO: 14:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: Protein (iii) HYPOTHETICAL: YES (iv) ANTI-SENSE: NO (xi) SEQUENCE DESCRIPTION: SEQ ID NO: 14:

```
Thr Arg Gly Ile Thr Cys Pro Pro Met Ser Val Glu His Ala Asp
  1               5                  10                  15

Ile Trp Val Lys Ser Tyr Ser Leu Tyr Ser Arg Glu Arg Tyr Ile Cys
                 20                  25                  30

Asn Ser Gly Phe Lys Arg Lys Ala Gly Thr Ser Ser Leu Thr Glu Cys
                 35                  40                  45

Val Leu Asn Lys Ala Thr Asn Val Ala His Trp Thr Thr Pro Ser Leu
 50                  55                  60

Lys Cys Ile Arg Asp Pro Ala Leu Val His Gln Arg Pro Ala Pro Pro
 65                  70                  75                  80

Ser Thr Val Thr Thr Ala Gly Val Thr Pro Gln Pro Glu Ser Leu Ser
                 85                  90                  95

Pro Ser Gly Lys Glu Pro Ala Ala Ser Ser Pro Ser Ser Asn Asn Thr
                100                 105                 110

Ala Ala Thr Thr Ala Ala Ile Val Pro Gly Ser Gln Leu Met Pro Ser
                115                 120                 125

Lys Ser Pro Ser Thr Gly Thr Thr Glu Ile Ser Ser His Glu Ser Ser
130                 135                 140

His Gly Thr Pro Ser Gln Thr Thr Ala Lys Thr Trp Glu Leu Thr Ala
145                 150                 155                 160

Ser Ala Ser His Gln Pro Pro Gly Val Tyr Pro Gln Gly His Ser Asp
                165                 170                 175

Thr Thr Val Ala Ile Ser Thr Ser Thr Val Leu Leu Cys Gly Leu Ser
                180                 185                 190

Ala Val Ser Leu Leu Ala Cys Tyr Leu Lys Ser Arg Ala Ser Val Cys
                195                 200                 205

Ser Cys His Pro Arg Ser Ala Gly His Thr Cys Ser Val Gly Ser Val
                210                 215                 220

Cys
225
```

(2) INFORMATION FOR SEQ ID NO: 15:

-continued

```
    (i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: Protein (iii) HYPOTHETICAL: YES (iv) ANTI-SENSE: NO (xi) SEQUENCE DESCRIPTION: SEQ ID NO: 15:

Met Ala Pro Arg Arg Ala Arg Gly Cys Arg Thr Leu Gly Leu Pro Ala
1               5                  10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Thr Trp Glu Leu Thr Ala Ser Val Ser His Gln
            180                 185                 190

Pro Thr Gly Val Phe Pro Gln Gly His Ser Asp Thr Thr Val Ala Ile
            195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265
```

INTERLEUKIN-15 RECEPTORS

CROSS REFERENCE TO RELATED APPLICATION

This application is a continuation of U.S. patent applicaton 08/988,197, filed Dec. 10, 1997, now U.S. Pat. No. 6,548,065, which is a continuation of U.S. patent application Ser. No. 08/435,760, filed May 4, 1995, now abandoned, which is a continuation-in-part application of U.S. patent application Ser. No. 08/300,903, filed Sep. 6, 1994, now U.S. Pat. No. 5,591,630, which is a continuation-in-part application of U.S. patent application Ser. No. 08/236,919, filed May 6, 1994, now abandoned.

BACKGROUND OF THE INVENTION

The present invention relates generally to cytokine receptors, and more specifically, to Interleukin-15 receptors.

Interleukin-15 (IL-15) is a recently identified cytokine with biological activities similar to IL-2 (Grabstein et al., *Science* 264:965, 1994). There is approximately 96% nucleotide sequence identity and 96% amino acid sequence identity between human and simian IL-15, and approximately 81% nucleotide sequence identity and 73% amino acid sequence identity between human and murine IL-15.

Northern analysis of a variety of human tissues indicated that IL-15 mRNA is expressed by many human tissues and abundantly by placenta and skeletal muscle. Significant levels of IL-15 mRNA were also observed in other tissues including kidney, lung, liver, and heart. The best sources of IL-15 mRNA so far observed have been adherent mononuclear cells (monocyte enriched, PBM) and epithelial and fibroblast cell lines such as CV-1/EBNA and IMTLH. Activated peripheral blood T cells (PBT), a rich source of IL-2, express no detectable IL-15 mRNA.

IL-15 shares many biological properties with Interleukin-2 ("IL-2"). These properties include proliferation and activation of human and murine T cells and the generation of lymphokine activated killer cells (LAK), natural killer cells (NK) and cytotoxic T lymphocytes (CTL). IL-15 also can co-stimulate with CD40 ligand (CD40L) proliferation and immunoglobulin secretion by B lymphocytes.

In view of the shared biological properties with IL-2, tests were conducted to determine whether IL-15 uses any of the components of the IL-2 receptor. IL-2 cell surface receptors (IL-2R) contain at least three subunits, $\alpha$, $\beta$ and $\gamma$ (Toshikazu et al., *Science*, 257: 379 (1992); see also Minami et al., *Annu. Rev. Immunol.* 11,245, 1993, for a recent review). The $\beta$ and $\gamma$ chains are required for high affinity IL-2 binding and IL-2 signaling and are members of the hematopoietin receptor superfamily. The $\alpha$ chain (or p55) is a low affinity, non-signaling binding subunit, and the only cytokine receptor member of a large family of binding proteins whose members include complement receptor proteins (Perkins et al., *Biochemistry* 27:4004, 1988; Davie et al., *Cold Spring Harb. Symp. Quant. Biol.* 51:509, 1986). The $\gamma$ chain of the IL-2R has been shown recently to be shared by receptors for several other cytokines (IL-4, IL-7, IL-9; (Noguchi et al., *Science* 262:1877, 1993; Kondo, et al., *Science* 262:1874, 1993; Kondo et al., *Science* 263:1453, 1994; Russell et al., *Science* 262:1880, 1993; Russell, et al., *Science* 266:1042, 1994) and designated the common $\gamma$ chain or $\gamma_c$.

Several lines of evidence suggest that there is an IL-15 specific binding protein. For example, an IL-3 dependent murine cell line, 32D (J. S. Greenberger et al., *Fed. Proc.* 42: 2762 (1983)), expressed the complete IL-2R and proliferated in response to IL-2, but cannot bind or respond to IL-15 (Grabstein et al., supra). Similarly, early murine pre-T cells derived from day 13 fetal liver that lack CD3, CD4 and CD8 expression (triple negative, or TN, cells) expressed all three IL-2R subunits, proliferated in response to IL-2, but did not bind or respond to IL-15 (Giri et al., *EMBO J.* 13:2822, 1994). On the other hand, certain human cell types and cell lines (e.g., umbilical vein endothelial cells, fibroblasts and thymic and stromal cells) did not bind IL-2 but bound IL-15 with high affinity (Giri et al., supra).

Additionally, antibodies directed against the a chain of the IL-2 receptor (anti-IL-2R$\alpha$) have no effect on IL-15 (Grabstein et al., supra; Giri et al., supra). Antibodies directed against the IL-2R$\beta$, however, are able to block the activity of IL-15, suggesting that IL-15 uses the B chain of IL-2R. Similarly, some cells require the $\gamma$ chain of IL-2R for IL-15 signal transduction (Giri et al., supra) IL-15 requires the $\beta$ chain of the IL-2R for all the biological activities tested, but the $\alpha$ chain of the IL-2R is not required (Giri et al., supra; Grabstein et al., supra). However, prior to the present invention, neither an IL-15-specific binding protein, nor a DNA encoding such protein, had been isolated.

SUMMARY OF THE INVENTION

The present invention provides isolated Interleukin-15 receptor (IL-15R) and isolated DNA sequences encoding IL-15R, in particular, human and murine IL-15R, or analogs thereof. Preferably, such isolated DNA sequences are selected from the group consisting of (a) DNA sequences comprising a nucleotide sequence derived from the coding region of a native IL-15R gene; (b) DNA sequences capable of hybridization to a DNA of (a) under moderate to high stringency conditions and that encode biologically active IL-15R; and (c). DNA sequences that are degenerate as a result of the genetic code to a DNA sequence defined in (a) or (b) and that encode biologically active IL-15R. The present invention also provides recombinant expression vectors or plasmids and transformed host cells comprising the DNA sequences defined above, recombinant IL-15R proteins produced using the recombinant expression vectors, plasmids or transformed host cells, and processes for producing the recombinant IL-15R proteins utilizing the expression vectors, plasmids or transformed host cells.

The present invention also provides substantially homogeneous preparations of IL-15R protein. The present invention also provides compositions for use in assays for IL-15 or IL-15R, purification of IL-15, or in raising antibodies to IL-15R, comprising effective quantities of the IL-15R proteins of the present invention.

These and other aspects of the present invention will become evident upon reference to the following detailed description.

BRIEF DESCRIPTION OF THE DRAWINGS

FIG. 2 presents a sequence alignment between the murine IL-15 receptor and the human IL15 receptor (clone W5). The top line represents the amino acid sequence of human IL-15R; the bottom line represents the amino acid sequence of murine IL-15R. The amino acid sequence has been separated into several protein domains:

Figure 1:
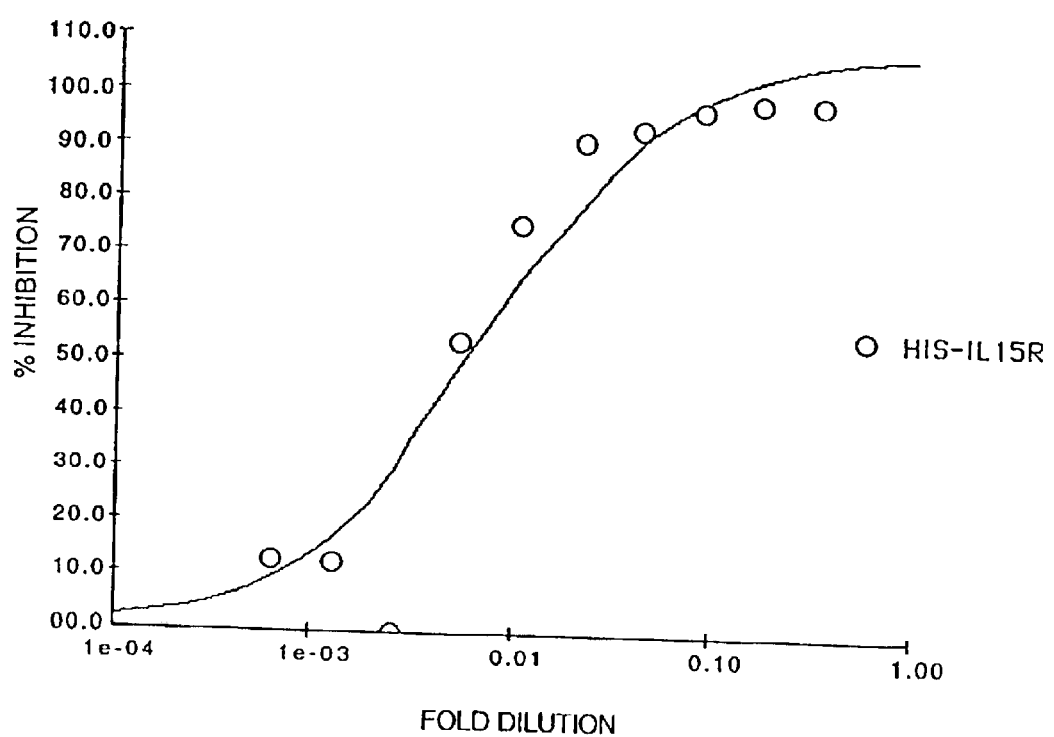
FIG. 1 illustrates the inhibition of binding of radiolabeled IL-15 to CTLL.2 cells by soluble murine IL-15 receptor (HIS-IL15R).

1. signal sequence
2. structural domain 1
3. proline-rich, flexible hinge region
4. structural domain 2
5. transmembrane domain
6. cytoplasmic domain The primary amino acid sequence was also analyzed for predicted structural characteristics, and found to share common features with a group of complement factors, and the α subunit of IL-2 receptor. Certain structural characteristics of the IL-15R are also designated in FIG. 2:

β: beta sheet
L: loop
bold: amino acids conserved among IL-15R and related proteins (i.e., complement control proteins, IL-2 receptor α chain)
shaded: putative IL-15 binding region

DETAILED DESCRIPTION OF THE INVENTION

"Interleukin-15 receptor," "IL-15R" and "IL-15Rα" refer to proteins that are present on many cell types, including cells of lymphoid origin, as well as non-lymphoid cells such as fresh human endothelial cells, and stromal cells types from bone marrow, fetal liver and thymic epithelium. As used herein, the above terms include analogs or fragments of native and recombinant IL-15R proteins with IL-15-binding activity. Specifically included are truncated, soluble or fusion forms of IL-15R protein as defined below. In the absence of any species designation, IL-15R refers generically to mammalian IL-15R, including but not limited to, human, murine, and bovine IL-15R. Similarly, in the absence of any specific designation for deletion mutants, the term IL-15R means all forms of IL-15R, including mutants and analogs that possess IL-15R biological activity.

"Soluble IL-15R" or "sIL-15R" as used in the context of the present invention refer to proteins, or substantially equivalent analogs, that are substantially similar to all or part of the extracellular region of a native IL-15R and are secreted by the host cell but retain the ability to bind IL-15. Soluble IL-15R proteins may also include part of the transmembrane region or part of the cytoplasmic domain or other sequences, provided that the soluble IL-15R proteins are capable of being secreted from the host cell in which they are produced.

The term "isolated" or "purified", as used in the context of this specification to define the purity of IL-15R protein or protein compositions, means that the protein or protein composition is substantially free of other proteins of natural or endogenous origin and contains less than about 1% by mass of protein contaminants residual of production processes. Such compositions, however, can contain other proteins added as stabilizers, carriers, excipients or co-therapeutics. IL-15R is purified to substantial homogeneity if no other proteins of natural or endogenous origin, or protein contaminants residual of production processes, are detected in a polyacrylamide gel by silver staining.

The term "substantially similar," when used to define either amino acid or nucleic acid sequences, means that a particular subject sequence, for example, a mutant sequence, varies from a reference sequence (e.g., a native sequence) by one or more substitutions, deletions, or additions, the net effect of which is to retain biological activity of the IL-15R protein as may be determined, for example, in IL-15R binding assays, such as is described in Example 1 below. Substantially similar analog protein will be greater than about 30 percent similar to the corresponding sequence of the native IL-15R. More preferably, the analog proteins will be greater than about 80 percent identical to the corresponding sequence of the native IL-15R. For fragments of IL-15R proteins, (e.g., soluble IL-15R polypeptides), the term "80 percent identical" refers to that portion of the reference native sequence that is found in the IL-15R fragment.

Computer programs are available for determining the percent identity between two DNA or amino acid sequences (e.g., between a mutant sequence and a native sequence). One example is the GAP computer program, version 6.0, described by Devereux et al., *Nucl. Acids Res.* 12:387 (1984) and available from the University of Wisconsin Genetics Computer Group (UWGCG). The GAP program uses the alignment method of Needleman and Wunsch, *J. Mol. Biol.* 48:443 (1970), as revised by Smith and Waterman, *Adv. Appl. Math* 2:482 (1981).

Alternatively, nucleic acid subunits and analogs are "substantially similar" to the specific native DNA sequences disclosed herein if (a) the DNA sequence is derived from the coding region of a native mammalian IL-15R gene; (b) the DNA sequence is capable of hybridization to a native IL-15R DNA sequence under moderately stringent conditions (i.e., 50° C., 2×SSC) and encodes biologically active IL-15R protein; or (c) the DNA sequence is degenerate as a result of the genetic code to one of the foregoing native or hybridizing DNA sequences and encodes a biologically active IL-15R protein. DNA sequences that hybridize to a native IL-15R DNA sequence under conditions of high stringency, and that encode biologically active IL-15R, are also encompassed by the present invention. Moderate and high stringency hybridization conditions are terms understood by the skilled artisan and have been described in, for example, Sambrook et al., *Molecular Cloning: A Laboratory Manual*, 2 ed. Vol. 1, pp. 1.101–104, Cold Spring Harbor Laboratory Press (1989). IL-15R proteins encoded by the foregoing DNA sequences are provided by the present invention.

"Recombinant DNA technology" or "recombinant", as used herein, refers to techniques and processes for producing specific polypeptides from microbial (e.g., bacterial, fungal or yeast) or mammalian cells or organisms (e.g., transgenics) that have been transformed or transfected with cloned or synthetic DNA sequences to enable biosynthesis of heterologous peptides. Native glycosylation patterns will only be achieved with mammalian cell expression systems. Yeast provide a distinctive glycosylation pattern. Prokaryotic cell expression (e.g., *E. coli*) will generally produce polypeptides without glycosylation.

"Biologically active", as used throughout the specification as a characteristic of IL-15R, means that a particular molecule shares sufficient amino acid sequence similarity with a native IL-15R protein to be capable of binding detectable quantities of IL-15, preferably with affinity similar to native IL-15R.

A "DNA sequence" refers to a DNA polymer, in the form of a separate fragment or as a component of a larger DNA construct, that has been derived from DNA isolated at least once in substantially pure form (i.e., free of contaminating endogenous materials) and in a quantity or concentration enabling identification, manipulation, and recovery of its component nucleotide sequences by standard biochemical methods such as those outlined in Sambrook et al., *Molecular Cloning: A Laboratory Manual*, 2nd ed., Cold Spring Harbor Laboratory, Cold Spring Harbor, N.Y. (1989). Such sequences are preferably provided in the form of an open reading frame uninterrupted by internal nontranslated sequences, or introns, that are typically present in eukaryotic genes. Sequences of non-translated DNA may be present 5' or 3' from an open reading frame, where the same do not interfere with manipulation or expression of the coding regions.

"Nucleotide sequence" refers to a heteropolymer of deoxyribonucleotides. DNA sequences encoding the proteins provided by this invention may be assembled from cDNA fragments and short oligonucleotide linkers, or from a series of oligonucleotides, to provide a synthetic gene that is capable of being expressed in a recombinant transcriptional unit.

"Recombinant expression vector" refers to a plasmid comprising a transcriptional unit comprising an assembly of (1) a genetic element or elements having a regulatory role in gene expression, for example, promoters or enhancers, (2) a structural or coding sequence that is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as E. coli or yeast such as S. cerevisiae, that has stably integrated a recombinant transcriptional unit into chromosomal DNA or carries the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of DNA Encoding IL-15R

As shown by Scatchard analysis of iodinated IL-15 binding, activated PBT as well as antigen specific T cell clones express only a few hundred receptors for IL-15. Cells from the murine Th2 CD4$^+$ cell clone, D10 (Kaye et al., *J. Immunol.* 133:1339 (1984)), express up to 24,000 IL-15 receptors when cultured with IL-2. A murine DNA sequence encoding murine IL-15R was isolated from a cDNA library prepared using standard methods by reverse transcription of polyadenylated RNA isolated from D10 cells. Transfectants expressing biologically active IL-15R were initially identified using a slide autoradiographic technique, substantially as described by Gearing et al., *EMBO J.* 8:3667 (1989).

A D10 cDNA library in plasmid pDC304 was prepared as described in Larsen et al., *J. Exp. Med.*, 172:159 (1990). pDC304 is derived from pDC302 previously described by Mosley et al., *Cell*, 59: 335–348 (1989) by deleting the adenovirus tripartite leader (TPL) in pDC302.

Using this approach, approximately 20,000 cDNAs were screened in pools of approximately 1000 cDNAs each using the slide autoradiographic method until assay of one transfectant pool showed multiple cells clearly positive for IL-15 binding. This pool was then partitioned into pools of approximately 100 and again screened by slide autoradiography and a positive pool was identified. Individual colonies from this pool of approximately 100 were screened until a single clone (clone D1-4-D5) was identified that directed synthesis of a surface protein with detectable L-15 binding activity. This clone was isolated and sequenced to determine the sequence of the murine IL-15R cDNA clone, D1-4-D5. The cloning vector pDC304 containing the murine IL-15R cDNA clone, D1-4-D5, was deposited with the American Type Culture Collection, 12301 Parklawn Drive, Rockville, Md. 20852 USA ("ATCC") in accordance with the Budapest Treaty on the International Recognition of the Deposit of Microorganisms for the Purposes of Patent Procedure on Apr. 22, 1994, under accession number ATCC 62659. The deposit was named "D1-4-D5 (pDC304:muIL-15R)" and comprised an E. coli strain containing a murine IL-15R cDNA insert that is made up of a 71-bp 5' noncoding region preceding an open reading frame of 792 bp and a 995-bp 3' non coding region (the 3'-most approximately 200 bp of which is likely to be derived from non-related sequence). The nucleotide sequence of the open reading frame is disclosed in SEQ ID NO: 1. All restrictions on the availability to the public of the material deposited will be irrevocably removed upon the granting of a patent.

A probe may be constructed from the murine sequence and used to screen various other mammalian cDNA libraries. cDNA clones that hybridize to the murine probe are then isolated and sequenced.

Like most mammalian genes, mammalian IL-15R is encoded by a multi-exon gene. IL-15R variants can be attributed to different mRNA splicing events following transcription or from proteolytic cleavage of the IL-15R protein, wherein the IL-15R binding property is retained. Alternative splicing of mRNA may yield a truncated but biologically active IL-15R protein, such as a soluble form of the protein. Variations attributable to proteolysis include, for example, differences in the N- or C-termini upon expression in different types of host cells, due to proteolytic removal of one or more terminal amino acids from the IL-15R protein (generally from 1–5 terminal amino acids). Signal peptides may be cleaved at different positions in a given protein, resulting in variations of the N-terminal amino acid of the mature protein. These IL-15R variants share large regions of identity or similarity with the cDNAs claimed herein and are considered to be within the scope of the present invention.

Proteins and Analogs

The present invention provides recombinant mammalian IL-15R polypeptides. Isolated IL-15R polypeptides of this invention are substantially free of other contaminating materials of natural or endogenous origin and contain less than about 1% by mass of protein contaminants residual of production processes. The IL-15R polypeptides of this invention are optionally without associated native-pattern glycosylation.

Mammalian IL-15R of the present invention includes, by way of example, primate, human, murine, canine, feline, bovine, ovine, equine and porcine IL-15R. The amino acid sequence of a full length murine IL-15R (i.e., including signal peptide, extracellular domain, transmembrane region and cytoplasmic domain) is shown in SEQ ID NOs: 1 and 2. The amino acid sequence in SEQ ID NOs: 1 and 2 predicts a type 1 membrane protein (i.e., a single transmembrane region with a N-terminal extracellular domain and a C-terminal cytoplasmic domain). The predicted signal peptide cleavage occurs between amino acids 30 and 31 in SEQ ID NO:2. The predicted transmembrane region includes amino acids 206 to 226 in SEQ ID NO:2. Mammalian IL-15R cDNA can be obtained by cross species hybridization, for example, by using a single stranded probe derived from the murine IL-15R DNA sequence, SEQ ID NO:1, as a hybridization probe to isolate IL-15R cDNAs from mammalian cDNA libraries. The isolated IL-15R cDNAs then can be transfected into expression vectors and host cells to express the IL-15R proteins.

Derivatives of IL-15R within the scope of the invention also include various structural forms of the primary protein that retain biological activity. Due to the presence of ionizable amino and carboxyl groups, for example, an IL-15R protein may be in the form of acidic or basic salts, or may be in neutral form. Individual amino acid residues may also be modified by oxidation or reduction.

The primary amino acid structure may be modified by forming covalent or aggregate conjugates with other chemical moieties, such as glycosyl groups, lipids, phosphate, acetyl groups and the like, or by creating amino acid sequence mutants. Covalent derivatives are prepared by linking particular functional groups to IL-15R amino acid side chains or at the N- or C-termini. Other derivatives of IL-15R within the scope of this invention include covalent or aggregative conjugates of IL-15R or its fragments with other proteins or polypeptides, such as by synthesis in recombinant culture as N-terminal or C-terminal fusions.

When initially expressed in a recombinant system, IL-15R may comprise a signal or leader polypeptide sequence (native or heterologous) at the N-terminal region of the protein. The signal or leader peptide co-translationally or post-translationally directs transfer of the protein from its site of synthesis to its site of function outside the cell membrane or wall, and is cleaved from the mature protein during the secretion process. Further, using conventional techniques, IL-15R polypeptides can be expressed as polypeptide fusions comprising additional polypeptide sequences, such as Fc or other immunoglobulin sequences, linker sequences, or other sequences that facilitate purification and identification of IL-15R polypeptides.

IL-15R derivatives may also be used as immunogens, reagents in receptor-based immunoassays, or as binding agents for affinity purification procedures of IL-15 or other binding ligands. IL-15R derivatives may also be obtained by cross-linking agents, such as m-maleimidobenzoyl succinimide ester and N-hydroxysuccinimide, at cysteine and lysine residues. IL-15R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, IL-15R may be used to selectively bind (for purposes of assay or purification) anti-IL-15R antibodies or IL-15.

The IL-15R proteins of the present invention encompass proteins having amino acid sequences that vary from those of native IL-15R proteins, but that retain the ability to bind IL-15. Such variant proteins comprise one or more additions, deletions, or substitutions of amino acids when compared to a native sequence, but exhibit biological activity that is essentially equivalent to that of native IL-15R protein. Likewise, the IL-15R-encoding DNA sequences of the present invention encompass sequences that comprise one or more additions, deletions, or substitutions of nucleotides when compared to a native IL-15R DNA sequence, but that encode an IL-15R protein that is essentially bioequivalent to a native IL-15R protein. Examples of such variant amino acid and DNA sequences (the "substantially similar" sequences discussed above) include, but are not limited to, the following.

Bioequivalent analogs of IL-15R proteins may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Another embodiment of the present invention involves modification of adjacent dibasic amino acid residues to enhance expression of IL-15R in yeast systems in which KEX2 protease activity is present. Generally, substitutions should be made conservatively; i. e., the most preferred substitute amino acids are those having physiochemical characteristics resembling those of the residue to be replaced. Similarly, when a deletion or insertion strategy is adopted, the potential effect of the deletion or insertion on biological activity should be considered.

Substantially similar polypeptide sequences, as defined above, generally comprise a like number of amino acid sequences, although C-terminal truncations for the purpose of constructing soluble IL-15Rs will contain fewer amino acid sequences. In order to preserve the biological activity of IL-15Rs, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian IL-15Rs are suggestive of additional conservative substitutions that may be made without altering the essential biological characteristics of IL-15R.

The present invention includes IL-15R with or without associated native-pattern glycosylation. IL-15R expressed in yeast or mammalian expression systems, e.g., COS-7 cells, may be similar or slightly different in molecular weight and glycosylation pattern than the native molecules, depending upon the expression system. Expression of IL-15R DNAs in bacteria such as E. coli provides non-glycosylated molecules. Functional mutant analogs of mammalian IL-15R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such sites can be eliminated by substituting another amino acid for Asn or for residue Z, deleting Asn or Z, or inserting a non-Z amino acid between $A_1$ and Z, or an amino acid other than Asn between Asn and $A_1$.

Subunits of IL-15R may be constructed by deleting terminal or internal residues or sequences. Particularly preferred sequences include those in which the transmembrane region and intracellular domain of IL-15R are deleted or substituted with hydrophilic residues to facilitate secretion of the receptor into the cell culture medium. Soluble IL-15R proteins may also include part of the transmembrane region, provided that the soluble IL-15R protein is capable of being secreted from the cell. The resulting protein is referred to as a soluble IL-15R molecule that retains its ability to bind IL-15. The present invention contemplates such soluble IL-15R constructs corresponding to all or part of the extracellular region of IL-15R. The resulting soluble IL-15R constructs are then inserted and expressed in appropriate expression vectors and assayed for the ability to bind IL-15, as described in Example 1. Biologically active soluble IL-15Rs (i.e., those which bind IL-15) resulting from such constructions are also contemplated to be within the scope of the present invention. Soluble IL-15Rs can be used to inhibit IL-15, for example, in ameliorating undesired effects of IL-15, in vitro or in vivo. For example, significant levels of IL-15 mRNA occur in kidney, lung, liver, and heart, organs that may be transplanted. Soluble IL-15Rs are thus likely to be useful as IL-15 antagonists in preventing or treating graft rejection. Soluble IL-15Rs can also be used as components of quantitative or qualitative assays for IL-15, or for affinity purification of IL-15.

Mutations in nucleotide sequences constructed for expression of the above-described variant or analog IL-15R proteins should, of course, preserve the reading frame phase of the coding sequences and preferably will not create complementary regions that could hybridize to produce secondary mRNA structures such as loops or hairpins that would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed IL-15R mutants screened for the desired activity.

Not all mutations in the nucleotide sequence that encodes IL-15R will be expressed in the final product. For example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression (see U.S. Pat. No. 4,425,437, column 6). The known degeneracy of the genetic code permits variation of a DNA sequence without altering the amino acid sequence, since a given amino acid may be encoded by more than one codon.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Examples of methods of making the alterations set forth above are disclosed by Walder et al., *Gene* 42:133 (1986); Bauer et al., *Gene* 37:73 (1985); Craik, *BioTechniques*, 12–19 (1985); Smith et al., *Genetic Engineering: Principles and Methods*, Plenum Press (1981); and U.S. Pat. Nos. 4,518,584 and 4,737,462.

The IL-15R proteins of the present invention encompass proteins encoded by (a) a DNA sequence derived from the coding region of a native IL-15R gene or (b) a DNA sequence capable of hybridization to a native IL-15R DNA of (a) under moderate to high stringency conditions and that encodes biologically active IL-15R. IL-15R proteins encoded by a DNA molecule that varies from the DNA sequences of SEQ ID NO:1, wherein one strand of the DNA molecule will hybridize to the DNA sequence presented in SEQ ID NO:1, include, but are not limited to, IL-15R fragments (soluble or membrane-bound) and IL-15R proteins comprising inactivated N-glycosylation site(s), inactivated KEX2 protease processing site(s), and/or conservative amino acid substitution(s), as described above. IL-15R proteins encoded by DNA derived from other mammalian species, wherein the DNA will hybridize to the murine DNA of SEQ ID NO:1, are also encompassed.

Both monovalent forms and polyvalent forms of IL-15R are useful in the compositions and methods of this invention. Polyvalent forms possess multiple IL-15R binding sites for IL-15 ligand. For example, a bivalent soluble IL-15R may consist of two tandem repeats of the extracellular region of IL-15R, separated by a linker region. Two IL-15R polypeptides (each capable of binding IL-15) may be joined by any suitable means, e.g., using one of the commercially available cross-linking reagents used to attach one polypeptide to another (Pierce Chemical Co., Rockford, Ill.). Alternatively, a fusion protein comprising multiple IL-15R polypeptides joined by peptide linkers may be produced using recombinant DNA technology. Suitable peptide linkers comprise a chain of amino acids, preferably from 20 to 100 amino acids in length. The linker advantageously comprises amino acids selected from the group consisting of glycine, asparagine, serine, threonine, and alanine. Examples of suitable peptide linkers and the use of such peptide linkers are found in U.S. Pat. No. 5,073,627.

Alternate polyvalent forms may also be constructed, for example, by chemically coupling IL-15R to any clinically acceptable carrier molecule, a polymer selected from the group consisting of Ficoll, polyethylene glycol or dextran using conventional coupling techniques. Alternatively, IL-15R may be chemically coupled to biotin, and the biotin-IL-15R conjugate then allowed to bind to avidin, resulting in tetravalent avidin/biotin/IL-15R molecules. IL-15R may also be covalently coupled to dinitrophenol (DNP) or trinitrophenol (TNP) and the resulting conjugate precipitated with anti-DNP or anti-TNP-IgM, to form decameric conjugates with a valency of 10 for IL-15R binding sites.

A recombinant chimeric antibody molecule may also be produced having IL-15R sequences substituted for the variable domains of either or both of the immunoglobulin molecule heavy and light chains and having unmodified constant region domains. For example, chimeric IL-15R/IgG$_1$ may be produced from two chimeric genes—an IL-15R/human K light chain chimera (IL-15R/CK) and an IL-15R/human γ1 heavy chain chimera (IL-15R/C$_{\gamma-1}$). Following transcription and translation of the two chimeric genes, the gene products assemble into a single chimeric antibody molecule having IL-15R displayed bivalently. Such polyvalent forms of IL-15R may have enhanced binding affinity for IL-15 ligand. Additional details relating to the construction of such chimeric antibody molecules are disclosed in WO 89/09622 and EP 315062.

Expression of Recombinant IL-15R

The present invention provides recombinant expression vectors to amplify or express DNA encoding IL-15R. Recombinant expression vectors are replicable DNA constructs that have synthetic or cDNA-derived DNA fragments encoding mammalian IL-15R or bioequivalent analogs operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence that is transcribed into mRNA and translated into protein, and (3) appropriate transcription and translation initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor that participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

DNA sequences encoding mammalian IL-15Rs that are to be expressed in a microorganism will preferably contain no introns that could prematurely terminate transcription of DNA into mRNA. However, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to SEQ ID NO:1 under at least moderately stringent conditions (50° C., 2×SSC) and other sequences hybridizing or degenerate to those that encode biologically active IL-15R polypeptides.

Recombinant IL-15R DNA is expressed or amplified in a recombinant expression system comprising a substantially homogeneous monoculture of suitable host microorganisms, for example, bacteria such as $E.$ $coli$ or yeast such as $S.$ $cerevisiae$, that have stably integrated (by transformation or transfection) a recombinant transcriptional unit into chromosomal DNA or carry the recombinant transcriptional unit as a component of a resident plasmid. Mammalian host cells are preferred for expressing recombinant IL-15R. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells that have been transformed or transfected with IL-15R vectors constructed using recombinant DNA techniques. Transformed host cells ordinarily express IL-15R, but host cells transformed for purposes of cloning or amplifying IL-15R DNA do not need to express IL-15R. Expressed IL-15R will be deposited in the cell membrane or secreted into the culture supernatant, depending on the IL-15R DNA selected. Suitable host cells for expression of mammalian IL-15R include prokaryotes, yeast or higher eukaryotic cells under the control of appropriate promoters. Prokaryotes include gram negative or gram positive organisms, for example $E.$ $coli$ or bacilli. Higher eukaryotic cells include established cell lines of mammalian origin as described below. Cell-free translation systems could also be employed to produce mammalian IL-15R using RNAs derived from the DNA constructs of the present invention. Appropriate cloning and expression vectors for use with bacterial, fungal, yeast, and mammalian cellular hosts are described by Pouwels et al., *Cloning Vectors: A Laboratory Manual*, Elsevier, N.Y. (1985).

Prokaryotic expression hosts may be used for expression of IL-15R that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include $E.$ $coli,$ $Bacillus$ $subtilis,$ $Salmonella$ $typhimurium,$ and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 and pGEX (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. $E.$ $coli$ is typically transformed using derivatives of pBR322, a plasmid derived from an $E.$ $coli$ species (Bolivar et al., *Gene* 2:95 (1977)). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615 (1978); and Goeddel et al., *Nature* 281:544 (1979)), the tryptophan (trp) promoter system (Goeddel et al., *Nucl. Acids Res.* 8:4057 (1980); and EPA 36,776) and tac promoter (Maniatis, *Molecular Cloning: A Laboratory Manual*, Cold Spring Harbor Laboratory, p. 412 (1982)). A particularly useful bacterial expression system employs the phage λ $P_L$ promoter and cI857ts thermolabile repressor. Plasmid vectors available from the American Type Culture Collection that incorporate derivatives of the λ $P_L$ promoter include plasmid pHUB2, resident in $E.$ $coli$ strain JMB9 (ATCC 37092) and pPLc28, resident in $E.$ $coli$ RR1 (ATCC 53082).

Recombinant IL-15R proteins may also be expressed in yeast hosts, preferably from the Saccharomyces species, such as $S.$ $cerevisiae.$ Yeast of other genera, such as Pichia or Kluyveromyces may also be employed. Yeast vectors will generally contain an origin of replication from the 2μ yeast plasmid or an autonomously replicating sequence (ARS), promoter, DNA encoding IL-15R, sequences for polyadenylation and transcription termination and a selection gene. Preferably, yeast vectors will include an origin of replication and selectable marker permitting transformation of both yeast and $E.$ $coli,$ e.g., the ampicillin resistance gene of $E.$ $coli$ and $S.$ $cerevisiae$ TRP1 or URA3 gene, that provides a selection marker for a mutant strain of yeast lacking the ability to grow in tryptophan, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil.

Suitable promoter sequences in yeast vectors include the promoters for metallothionein, 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968); and Holland et al., *Biochem.* 17:4900 (1978)). Suitable vectors and promoters for use in yeast expression are further described in R. Hitzeman et al., EPA 73,657.

Preferred yeast vectors can be assembled using DNA sequences from pUC18 for selection and replication in $E.$ coli (Amp$^r$ gene and origin of replication) and yeast DNA sequences including a glucose-repressible ADH2 promoter and α-factor secretion leader. The ADH2 promoter has been described by Russell et al., *J. Biol. Chem.* 258:2674 (1982) and Beier et al., *Nature* 300:724 (1982). The yeast α-factor leader, that directs secretion of heterologous proteins, can be inserted between the promoter and the structural gene to be expressed (see, e.g., Kurjan et al., Cell 30:933 (1982); and Bitter et al., *Proc. Natl. Acad. Sci. USA* 81:5330 (1984)). The leader sequence may be modified to contain, near its 3' end, one or more useful restriction sites to facilitate fusion of the leader sequence to foreign genes. Suitable yeast transformation protocols are known to those of skill in the art (see Hinnen et al., *Proc. Natl. Acad. Sci. USA* 75:1929 (1978); Sherman et al., *Laboratory Course Manual for Methods in Yeast Genetics*, Cold Spring Harbor Laboratory, Cold Spring Harbor, N.Y. (1986)).

Host strains transformed by vectors comprising the ADH2 promoter may be grown for expression in a rich medium consisting of 1% yeast extract, 2% peptone, and 1% or 4% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express recombinant protein. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman, *Cell* 23:175 (1981), and other cell lines capable of expressing a heterologous gene in an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment that also contains the SV40 viral origin of replication (Fiers et al., *Nature* 273:113 (1978)). Smaller or larger SV40 fragments may also be used, provided the approximately 250 bp sequence extending from the Hind III site toward the BglI site located in the viral origin of replication is included. Further, mammalian genomic IL-15R promoter, control and/or signal sequences may be used, provided such control sequences are compatible with the host cell chosen. Exemplary vectors can be constructed as disclosed by Okayama and Berg, *Mol. Cell. Biol.* 3:280 (1983).

A useful system for stable high level expression of mammalian receptor cDNAs in C127 murine mammary epithelial cells can be constructed substantially as described by Cosman et al., *Mol. Immunol.* 23:935 (1986).

In preferred aspects of the present invention, recombinant expression vectors comprising IL-15R cDNAs are stably integrated into a host cell's DNA. Elevated levels of expression product are achieved by selecting for cell lines having amplified numbers of vector DNA. Cell lines having amplified numbers of vector DNA are selected, for example, by transforming a host cell with a vector comprising a DNA sequence that encodes an enzyme that is inhibited by a known drug. The vector may also comprise a DNA sequence that encodes a desired protein. Alternatively, the host cell may be co-transformed with a second vector that comprises the DNA sequence that encodes the desired protein. The transformed or co-transformed host cells are then cultured in increasing concentrations of the known drug, thereby selecting for drug-resistant cells. Such drug-resistant cells survive in increased concentrations of the toxic drug by overproduction of the enzyme that is inhibited by the drug, frequently as a result of amplification of the gene encoding the enzyme. Where drug resistance is caused by an increase in the copy number of the vector DNA encoding the inhibiting enzyme, there is a concomitant co-amplification of the vector DNA encoding the desired protein (e.g., IL-15R) in the host cell's DNA.

A preferred system for such co-amplification uses the gene for dihydrofolate reductase (DHFR), that can be inhibited by the drug methotrexate (MTX). To achieve co-amplification, a host cell that lacks an active gene encoding DHFR is either transformed with a vector that comprises DNA sequence encoding DHFR and a desired protein, or is co-transformed with a vector comprising a DNA sequence encoding DHFR and a vector comprising a DNA sequence encoding the desired protein. The transformed or co-transformed host cells are cultured in media containing increasing levels of MTX, and those cell lines that survive are selected.

A particularly preferred co-amplification system uses the gene for glutamine synthetase (GS), that is responsible for the synthesis of glutamine from glutamate and ammonia using the hydrolysis of ATP to ADP and phosphate to drive the reaction. GS is subject to inhibition by a variety of inhibitors, for example methionine sulphoximine (MSX). Thus, IL-15R can be expressed in high concentrations by co-amplifying cells transformed with a vector comprising the DNA sequence for GS and a desired protein, or co-transformed with a vector comprising a DNA sequence encoding GS and a vector comprising a DNA sequence encoding the desired protein, culturing the host cells in media containing increasing levels of MSX and selecting for surviving cells. The GS co-amplification system, appropriate recombinant expression vectors and cells lines, are described in the following PCT applications: WO 87/04462, WO 89/01036, WO 89/10404 and WO 86/05807.

Recombinant proteins are preferably expressed by co-amplification of DHFR or GS in a mammalian host cell, such as Chinese Hamster Ovary (CHO) cells, or alternatively in a murine myeloma cell line, such as SP2/0-Ag14 or NS0 or a rat myeloma cell line, such as YB2/3.0-Ag20, disclosed in PCT applications WO 89/10404 and WO 86/05807.

Vectors derived from retroviruses may be employed in mammalian host cells. A preferred retroviral expression vector is tgLS(+) HyTK, described in PCT application WO 92/08796.

A preferred eukaryotic vector for expression of IL-15R DNA is disclosed below in Example 1. This vector, referred to as pDC304, was derived from pDC302 previously described by Mosley et al., *Cell*, 59: 335–348 (1989) by deleting the adenovirus tripartite leader in pDC302.

Sense and Antisense Sequences

The present invention provides both double-stranded and single-stranded IL-15R DNA, and IL-15R mRNA as well. The single-stranded IL-15R nucleic acids have use as probes to detect the presence of hybridizing IL-15R nucleic acids (e.g., in in vitro assays) and as sense and antisense molecules to block expression of IL-15R.

In one embodiment, the present invention provides antisense or sense molecules comprising a single-stranded nucleic acid sequence (either RNA or DNA) capable of binding to target IL-15R mRNA (sense) or IL-15R DNA (antisense) sequences. These antisense or sense molecules may comprise a fragment of the coding region of IL-15R cDNA, and, in one embodiment, are oligonucleotides comprising at least about 14 nucleotides, preferably from about 14 to about 30 nucleotides, of an IL-15R cDNA sequence. The ability to create an antisense or sense oligonucleotide based upon a cDNA sequence for a given protein is described in, for example, Stein and Cohen, *Cancer Res.* 48:2659 (1988) and van der Krol et al., *BioTechniques* 6:958 (1988).

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The oligonucleotides thus may be used to block expression of IL-15R proteins. Uses of the antisense and sense nucleic acid sequences include, but are not limited to, use as research reagents. The biological effects of blocking IL-15R expression in cultured cells may be studied, for example. The oligonucleotides also may be employed in developing therapeutic procedures that involve blocking IL-15R expression in vivo.

Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are relatively stable in vivo (i.e., capable of resisting enzymatic degradation) but retain sequence specificity for binding to target nucleotide sequences. Other examples of sense or antisense oligonucleotides include those oligonucleotides that are covalently linked to organic moieties such as those described in WO 90/10448, or to other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any suitable method, including, for example, $CaPO_4$-mediated DNA transfection, electroporation, or by using gene transfer vectors such as Epstein-Barr virus. A preferred method involves insertion of the antisense or sense oligonucleotide into a suitable retroviral vector, then contacting the target cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by attaching the oligonucleotide to a molecule that binds to the target cell, as described in WO 91/04753. The oligonucleotide may be attached to molecules that include, but are not limited to, antibodies, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLES

Example 1

Isolation and Expression of cDNAs Encoding Murine IL-15R

A. Radiolabeling of IL-15. Recombinant flag simian IL-15 expressed in yeast (SEQ ID NO:3) was purified by passage over a Phenyl Sepharose CL-4B column (Pharmacia, Piscataway, N.J.) followed by two passages over reverse phase HPLC C4 columns (Vydac), the first using a pyridine acetate/propanol buffer system, the second in trifluoro-acetic acid acetonitrile system. Fractions containing pure IL-15 were dried under nitrogen and radiolabeled using the enzymobead iodination reagent (BioRad, Richmond Va.) as described by in Park et al., *J. Exp. Med.*, 165:1201–1206 (1987). The biological activity of radiolabeled IL-15 was assessed using the mitochondrial stain MTT (3-4,5-Dimethylthiazol-2-yl)-2,5-diphenyl tetrazolium bromide; thiazol blue (Sigma, St. Dextran, as described by Cosman et al., *Nature*, 312:768–771 (1984)).

B. Binding To Intact Cells. A source for IL-15R was selected by screening various murine and human cells lines and tissues for expression of IL-15R based on their ability to bind $^{125}$I-IL-15 that was prepared as described above in Example 1A. For the binding assays, a phthalate oil separation method (Dower et al., *J. Immunol.* 132:751 (1984)) was performed as described by Park et al., *J. Biol. Chem* 261:4177 (1986) and Park et al., *Proc. Natl. Acad. Sci. USA* 84:5267 (1987) on candidate cells grown in suspension culture. Nonspecific binding of $^{125}$I-IL-15 was measured in the presence of a 200-fold or greater molar excess of unlabeled IL-15. Sodium azide (0.2%) was included in all binding assays to inhibit internalization of $^{125}$I-IL-15 at 37° C. Activated PBT and well as antigen specific T cell clones expressed only a few hundred receptors for IL-15. Cells from the murine Th2 CD4$^+$ cell clone, D10 (Kaye et al., *J. Immunol.*, 133:1339 (1984)), expressed up to 24,000 IL-15 receptors when cultured with IL-2.

C. Construction and Screening of cDNA Library. Polyadenylated mRNA was prepared from a D10 cell line and cDNAs were prepared using standard techniques. The D10 line is a producer of murine IL-15R. cDNA ends were adapted with BglII adaptors:

5'-GATCTTGGAACGAGACGACCTGCT-3' (SEQ ID NO:4)
3'-AACCTTGCTCTGCTGGACGA-5' (SEQ ID NO:5)
and cloned into vector pDC304.

COS-7 cells were transfected with miniprep DNA from pools of cDNA clones directly on glass slides and cultured for 2–3 days to permit transient expression of IL-15R. The slides containing the transfected cells were then incubated with medium containing $^{125}$I-labeled IL-15, washed to remove unbound labeled IL-15, fixed with glutaraldehyde, and dipped in liquid autoradiographic emulsion and exposed in the dark. After developing the slides, they were individually examined with a microscope and positive cells expressing IL-15R were identified by the presence of autoradiographic silver grains against a light background. Approximately 20,000 cDNAs were screened in pools of approximately 1000 cDNAs each using the slide autoradiographic method until assay of one transfectant pool showed multiple cells clearly positive for IL-15 binding. This pool was then partitioned into pools of approximately 100 and again screened by slide autoradiography and a positive pool was identified. Individual colonies from this pool of approximately 100 were screened until a single clone (clone D1-4-D5) was identified that directed synthesis of a surface protein with detectable IL-15 binding activity. This clone was isolated and sequenced to determine the sequence of the murine IL-15R cDNA clone, D1-4-D5. The cloning vector pDC304 containing the murine IL-15R cDNA clone, D1-4-D5, was deposited with the American Type Culture Collection ("ATCC") under accession number ATCC 62659. The murine IL-15R cDNA insert is made up of a 71-bp 5' noncoding region before an open reading frame of 792 bp and a 995-bp 3' non coding region. The nucleotide sequence of the open reading frame is disclosed in SEQ ID NO:1. The amino acid sequence of a full length murine IL-15R (i.e., including signal peptide, extracellular domain, transmembrane region and cytoplasmic domain) is shown in SEQ ID NOs:1 and 2. The amino acid sequence in SEQ ID NOs:1 and 2 predicts a type 1 membrane protein (i.e., a single transmembrane region with a N-terminal extracellular domain and a C-terminal cytoplasmic domain). A predicted signal peptide cleavage occurs between amino acids 30 and 31 in SEQ ID NO:2; amino acids 32 and 33 are predicted to form another, preferred, cleavage site. The predicted transmembrane region includes amino acids 206 to 226 in SEQ ID NO:2.

D. Recombinant IL-15R Binding. Plasmid DNA from IL-15 receptor expression plasmid was used to transfect a sub-confluent layer of monkey COS-7 cells using DEAE-dextran followed by chloroquine treatment, as described by Luthman et al., *Nucl Acids Res.* 11:1295 (1983) and McCutchan et al., *J. Natl. Cancer Inst.* 41:351 (1968). The cells were then grown in culture for three days to permit transient expression of the inserted sequences. After three days, the cell monolayers were assayed for $^{125}$1-IL-15 binding essentially as described by Park, et al., *J. Exp. Med.* 166:476 (1987). Non-specific binding of $^{125}$I-L-15 was measured in the presence of 200-fold or greater excess of unlabeled IL-15. Initial binding studies of $^{125}$I-IL-15 to COS cells transfected with IL-15R cDNA clone D1-4-D5 showed very high levels of expression (~500,000 sites/cell), with an estimated affinity of 1.0–2.2 nM, which is much lower that the affinity of the native receptor on D10 cells.

E. Soluble IL-15R. A soluble murine IL-15 receptor was prepared by deleting the transmembrane and cytoplasmic domains, with the C-terminal end corresponding to Thr at amino acid 204 of SEQ ID NO:1, and adding 5 C-terminal Histidines. The soluble IL-15 receptor was biologically active, as demonstrated by the fact that it inhibited binding of radiolabeled IL-15 to cells expressing membrane bound IL-15 receptor (FIG. 1).

Example 2

Preparation of Monoclonal Antibodies to IL-15R

Preparations of purified recombinant IL-15R, for example, human IL-15R, or transfected COS cells expressing high levels of IL-15R are employed to generate monoclonal antibodies against IL-15R using conventional techniques, for example, those disclosed in U.S. Pat. No. 4,411,993. Such antibodies are likely to be useful in interfering with IL-15 binding to IL-15R, for example, in ameliorating undesired effects of IL-15, or as components of diagnostic or research assays for IL-15 or soluble IL-15R.

To immunize mice or rats, IL-15R immunogen is emulsified in complete Freund's adjuvant and injected in amounts ranging from 10–100 μg, subcutaneously. Ten to twenty-one days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused with an appropriate murine myeloma cell line. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with IL-15R, for example, by adaptations of the techniques disclosed by Engvall et al., *Immunochem.* 8:871 (1971) and in U.S. Pat. No. 4,703,004. Clones that produce antibodies that bind IL-15R and inhibit binding of IL-15 to IL-15R (blocking or neutralizing antibodies) can also be isolated. Positive clones are then injected into the peritoneal cavities of syngeneic animals to produce ascites containing high concentrations (>1 mg/ml) of anti-IL-15R monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 3

Isolation and Expression of cDNAs Encoding Human IL-15R

A. Binding of IL-15 to Human Cells

Various human cell lines and tissues were screened for the ability to bind radiolabeled IL-15 substantially as described in Example 1. High affinity binding was observed on activated peripheral blood mononuclear cells, activated monocytes and some EBV-transformed cell lines. High affinity binding was also measured on human fibroblast lines such as W126-VA4 (ATCC CCL 95.1; Kd: 27 pM; 1,400 sites per cell), a glioblastoma cell line, A-172 (ATCC CRL 1620; Kd 50–138 pM; 1,560–4,350 sites pre cell), and vascular endothelial cells (both venous and arterial origin, Kd 33 pM, 990 sites per cell; Kd 163 pM, 1,920 sites per cell, respectively). Cross-linking of radiolabeled IL-15 to receptors present on the surface of A172 cells showed a major IL-15 binding protein with an estimated molecular weight of 55–65 Kd, a size similar to that seen on the D10 murine cell line by cross-linking.

B. Clone W5

A cDNA encoding human IL-15R was isolated by cross-species hybridization of the murine IL-15R cDNA to a human cDNA library prepared from the human cell line W126-VA4-VA4 in the bacteriophage λgt10 vector. Preparation of the library is described in U.S. Pat. No. 5,194,375, issued Mar. 16, 1993 (DNAs Encoding IL-7 Receptors). The W126-VA4 library was screened with a random prime labeled murine IL-15R cDNA probe in 50% formamide buffer (50% formamide, 5×SSC, 20 mM EDTA, 2×Denhardt's, 1% SDS, 0.1% sarcosyl, 50 mM KHPO$_4$ pH 6.5, 300 μg/ml salmon sperm DNA) using 1×10$^6$ cpm of probe/ml of hybridization solution, at 42° C. for 16–20 hours. The filters were washed once with 6×SSC/0.1% SDS at room temperature, followed by several moderate stringency washes in 2×SSC/0.1% SDS at 55° C.

Approximately 500,000 plaques of the amplified λgt100/W126-VA4 library were screened by standard methods, using the random-prime labeled murine IL-15R probe, which contained the entire coding region as well as 5' and 3' flanking non-coding regions. A single hybridizing plaque was identified, plaque-purified, and its cDNA insert amplified by PCR, purified, and sequenced. This clone, designated 'W5,' shared about 65% identity at the nucleotide level and 56% identity at the amino acid level with the murine cDNA, 'D1-4-D5' (SEQ ID NO: 1). The nucleotide and predicted amino acid sequence of W5 are shown in SEQ ID NOs:6 and 7.

As compared to the full-length murine clone D1-4-D5, W5 appeared to be missing a small portion of the expected 5' sequences, i.e., about 125 bp compared to the murine clone, indicating that W5 did not contain the coding region for the first part of a putative IL-15R signal peptide (missing 19 amino acids compared to the murine clone). The amino acid sequence in SEQ ID NOs:6 and 7 predicts a type 1 membrane protein (i.e., a single transmembrane region with an N-terminal extracellular domain and a C-terminal cytoplasmic domain). The predicted transmembrane region includes amino acids 190 to 210 of SEQ ID NOs:6 and 7. Binding of IL-15R to IL-15 is mediated through the extracellular domain of IL-15R as shown in FIG. 2, all or portions of which are involved in binding.

A signal peptide cleavage is predicted to occur between amino acids 14 and 15 in SEQ ID NO:6. For murine IL-15 receptor, a signal peptide cleavage is predicted to occur between amino acids 32 and 33 in SEQ ID NO:2, or alternatively, between amino acids 30 and 31 in SEQ ID NO:2. Because of the similarity between murine and human IL-15 receptor in this region, and because the murine IL-7 leader sequence (see below) utilizes a Thr residue as the mature N-terminal amino acid following the leader, the Thr at residue 12 of SEQ ID NOs:6 and 7 was chosen as the mature N-terminus of a human IL-15 receptor construct.

The mature peptide coding domain of W5 (nucleotides 34 through 753 of SEQ ID NO:6), and the remaining 3' non-coding sequence, was fused to the coding domain for the signal peptide of murine IL-7 in the expression vector pDC206 (similar to pDC201, described in Sims et al., *Science* 241: 585, 1988, with the addition of the murine IL-7 leader sequence, which is described in U.S. Pat. No. 4,965, 195, issued Oct. 23, 1990). Transfection of this recombinant plasmid into COS-7 cells followed by cell-surface binding of radiolabeled human IL-15 substantially as described in Example 1 showed that this plasmid encoded a biologically active polypeptide, i.e., one which bound L-15. The clone W5 construct containing the murine IL-7 leader sequence in pDC206 was deposited with the American Type Culture Collection ("ATCC", 12301 Parklawn Dr., Rockville, Md. 20852, USA), under the conditions of the Budapest Treaty on Sep. 1, 1994, and given accession number ATCC 69690.

C. Clone P1

A λgt10 library from human peripheral blood lymphocytes, prepared as described in U.S. Ser. No. 08/094, 669, filed Jul. 20, 1993, and in Idzerda et al., *J. Exp. Med.* 171:861 (1990), was screened for the presence of a full-length clone encoding human IL-15R using a random prime labeled human IL15R cDNA probe consisting of the entire W5 cDNA without the poly-A tail (which had been removed by digestion of the cDNA with Ssp I followed by gel purification of the remaining fragment, resulting in a fragment of approximately 1465 bp), using substantially the same conditions as described for screening of the A172 library (described below). The resulting sequence of the cDNA insert from this clone (SEQ ID NOs:8 and 9) exhibited an in-frame insertion of 153 basepairs at the mature N-terminus (amino acids 24 through 74 of SEQ ID NOs:8 and 9), an in-frame deletion of 99 basepairs downstream of the mature N-terminus that deleted nucleotides 236 through 334 of SEQ ID NO:6 (the sequence encoding amino acids 79 though 112, with the substitution of a Lys residue encoded by the codon AAG, the equivalent of nucleotides 235, 335 and 336 of SEQ ID NO:6), and also contained additional 5' sequence as compared to clone W5 (amino acids 1 though 10 of SEQ ID NOs:8 and 9), but still did not contain an initiator Met.

D. Clone A212

A library prepared from A172 cells as described in U.S. Ser. No. 08/265,086, filed Jun. 17, 1994, was screened for the presence of a full-length clone encoding human IL-15R. DNA (1–5 μg) from library pools (approximately 1000 cDNA clones/pool) was digested with Sal I to release the inserted DNA, electrophoresed (1% agarose, Tris-borate gel), and blotted to a nylon membrane. The blot was probed with a random prime labeled human IL15R cDNA probe consisting of the entire W5 cDNA minus the poly A tail, under conditions of high stringency (50% formamide, 42° C. hybridization for 16–20 hr, followed by washing at 2×SSC at room temperature for 5 minutes followed by 0.1×SSC/0.1% SDS at 68° C.). The blot was autoradiographed, and a pool with a positive signal (i.e. hybridizing band) was chosen for isolation of individual clones by colony hybridization.

A portion of the frozen glycerol stock of the pool of cDNA clones corresponding to the Southern blot signal was diluted and plated onto appropriate plates (LB+ampicillin). Colonies were lifted onto nylon membranes and the membranes processed using standard techniques. The membranes were hybridized and washed under stringent conditions as described above, and a colony corresponding to a positive hybridizing signal was grown, its plasmid DNA purified and sequenced. The resulting sequence of the cDNA insert from this clone (SEQ ID NOs: 10 and 11) exhibited the same in-frame deletion of 99 basepairs downstream of the mature N-terminus as clone P1 (a deletion of nucleotides 236 through 34 of SEQ ID NO:6, the sequence encoding amino acids 79 though 112, with the substitution of a Lys residue encoded by the codon AAG, the equivalent of nucleotides 235, 335 and 336 of SEQ ID NO:6). The plasmid was transfected into COS cells, and the ability of the encoded protein to bind IL-15 determined using slide autoradiography with $^{125}$I-labeled human IL-15 substantially as described in Example 1. Clone A212 also encoded a biologically active polypeptide, i.e., one which bound IL-15. Additionally, clone A212 exhibited a complete signal peptide as compared to clone W5, as indicated by the presence of additional 5' sequence and an initiator Met.

E. Clone A133

A second clone was isolated from the A172 library described above, under substantially the same conditions. The nucleotide and amino acid sequence of the A133 clone are shown in SEQ ID NOs:12 and 13. This clone exhibited an incomplete 5' region which began at the equivalent of nucleotide 355 of clone W5 (SEQ ID NO:6), and an in-frame insertion downstream of the transmembrane region that results in a different cytoplasmic tail coding domain (amino acids 97 through 117 of SEQ ID NOs:12 and 13). A hybrid construct encoding the 5' half of W5 fused to A133 to give the alternate cytoplasmic tail (SEQ ID NO: 14) was prepared, and expressed substantially as described above for clone WS. Cell-surface binding experiments using radiolabeled human IL-15 substantially as described in Example 1 showed that this hybrid construct encoded a polypeptide that bound IL-15.

SEQ ID NO: 15 presents the predicted amino acid sequence of a composite human IL-15R containing the signal peptide of clone A212 and the coding region of clone W5. SEQ ID NO: 15 also contains an Xaa at amino acid 182, wherein Xaa is Asn or Thr. Clones W5 and P1 contain a Thr at the equivalent position (W5: amino acid 166 of SEQ ID NOs:6 and 7; P1: amino acid 194 of SEQ ID NOs:8 and 9), whereas clones A212 and A133 contain an Asn at the equivalent position (A212: amino acid 149 of SEQ ID NOs:10 and 11; A133: amino acid 48 of SEQ ID NOs: 13 and 14). The Asn/Thr substitution does not affect binding of IL-15, as evidenced by the fact that both clones W5 and A212 encoded a peptide that bound IL-15, and may be due to allelic variation.

Example 4

Characterization of the Role of the α Subunit of the IL-15R

A. Functional Role for the α Subunit of the IL-15R on Murine Cells

In initial binding experiments with COS-7 cells transfected with the murine IL-15Ra cDNA clone D5, in excess of $5\times10^5$ receptors/cell were detected, a level too high to obtain accurate measurements of IL-15 binding to these cells. More accurate measurements of the affinity of IL-15Rα for IL-15 were obtained using the murine IL-3 dependent 32D cell line, which constitutively expresses the IL-2R α and $\gamma_c$ chains, but failed to respond to IL-15 (Grabstein, et al., 1994, supra) as a model system. 32D cells stably expressing various components of the IL-2 and IL-15 receptors were derived and tested for their ability to proliferate in response to IL-15.

The original 32D cell line responded to IL-2, but a subline, 32D-01, which had lost the ability to respond to IL-2 (presumably because it no longer expressed sufficient levels of IL-2Rβ) was used in these experiments. The murine IL-2Rβ chain was introduced into 32D-01, resulting in a line designated 32Dmβ-S, which had the ability to proliferate in response to IL-2 but not IL-15. No detectable IL-15 binding to 32D-01 or 32Dmβ-5 was seen by cytofluorometric analysis, suggesting that the level of IL-15Rα was very low on these cells. Direct binding with $^{125}$I-IL-15 confirmed this result (see below).

To test the role of IL-15Rα, 32D-01 cells were transfected with the IL-15Rα cDNA, which resulted in a line expressing the α chain, 32Dm15Rα-102. Although these cells bound high levels of IL-15 as evidenced by both cytofluorometric analysis and radiolabeled IL-15 binding, they were unable to proliferate in response to IL-15. The 32Dm15Roα-102 cells, like the parental 32D-01, did not express detectable levels of IL-2Rβ. A cell line termed 32Dmβm15Rα-3, co-expressing both IL-15Rα and IL-2Rβ ($\gamma_c$ is constitutively expressed) was derived, which was able to proliferate in response to IL-15 and IL-2, with a pattern similar to proliferation of the D10 cell line (from which D1-4-D5 ["DS"] was cloned). This result demonstrates that the ability of murine cells to respond to simian IL-15 is dependent on the level of IL-15Rα expression and confirms the requirement for IL-2Rβ.

B. IL-15Rα binds IL-15 with High Affinity

Preliminary equilibrium binding experiments with $^{125}$I-simian IL-15 indicated that the IL-15Rα chain alone was binding IL-15 with very high affinity; therefore, the optimal binding conditions necessary to accurately measure this affinity under equilibrium conditions, as well as to measure whether a receptor complex containing the β and $\gamma_c$ chains along with the IL-15Rα chain exhibited an enhanced affinity for IL-15, were assessed. The parental 32D-01 cell line expressed an average of 100+33 IL-15 binding sites per cell, with an affinity ($K_a$) of $1.4\pm0.4\times10^{11}$ M$^{-1}$, which is similar to the affinity of IL-2 binding to the IL-2Rα/β/$\gamma_c$ complex. The 32Dm15Rα-102 cells, transfected with the IL-15Rα chain, exhibited a much higher level of IL-15 binding with the same very high affinity (average of 15300±3700 sites per cell with a $K_a$ of $1.5\pm0.9\times10^{11}$ M$^{-1}$). Given the low expression of IL-2Rβ on these cells, the majority of these sites must reflect binding to the IL-15Rα chain alone. This suggests that the low amount of IL-15 binding on the 32D-01 cells is due to endogenous IL-15Rα.

The affinity of the receptors on both of these 32D lines is very similar to the affinity of the native IL-15R on the D10 cells from which the IL-15Rα subunit was cloned (average $K_a$ of $1.3\pm0.5\times10^{11}$ M$^{-1}$). Although D10 cells express several hundred copies of IL-2Rβ, inferred from the number of high affinity IL-2 binding sites (~500 sites/cell), a second component of binding in these cells which might correspond to a higher affinity α/β or α/β/$\gamma_c$ complex was not detected. This result was substantiated by analysis of the 32Dmβm15Rα-3 cells, co-expressing both recombinant IL-15Rot and IL-2Rβ subunits. These cells showed binding characteristics very similar to those exhibited by the 32Dm15Rα-102 cells, with an average $K_a$ of $2.2\pm0.3\times10^{11}$ M$^{-1}$, and 12800±2700 receptors/cell.

In both D10 and 32Dmβm15Rα-3 cells, overexpression of the IL-15Rα relative to the β subunit might serve to obscure a small higher affinity component. This possibility was addressed by analyzing binding to the 32Dmβ-5 cell line, which had been transfected with the β subunit alone. These cells showed a single high affinity binding site that was essentially identical to the parental 32D-01 line, with an average $K_a$ of $1.9\pm0.5\times10^{11}$ M$^{-1}$ and 40±15 sites per cell, presumably due to low level expression of endogenous IL-15Rα. The observation that the 32Dmβ-5 cell line did not display any additional IL-15 binding sites relative to the 32D-01 parent line indicated that simian IL-15 is unable to bind with any detectable affinity to complexes of murine β and $\gamma_c$, in the absence of the IL-15Rα chain.

What is claimed is:

1. An isolated DNA encoding an IL-15 receptor (IL-15R), wherein the DNA is selected from the group consisting of:
   (a) a DNA having a nucleotide sequence as set forth in SEQ ID NO:1, nucleotides 91 through 789;
   (b) a DNA having a nucleotide sequence as set forth in SEQ ID NO:6, nucleotides 34 through 753;
   (c) DNAs that hybridize to the DNA sequences of (a) or (b) or their complementary strands under conditions of moderate stringency (50° C., 2×SSC), and which encode polypeptides capable of binding IL-15; and
   (d) DNAs that, due to degeneracy of the genetic code, encode polypeptides encoded by any of the foregoing DNAs.

2. An isolated DNA according to claim 1 that encodes a human IL-15R.

3. An isolated DNA according to claim 1 that encodes a soluble IL-15R.

4. An isolated DNA according to claim 3 wherein the DNA is selected from the group consisting of:
   (a) a DNA having a nucleotide sequence as set forth in SEQ ID NO:1, nucleotides 91 through 612;

(b) a DNA having a nucleotide sequence as set forth in SEQ ID NO:6, nucleotides 34 through 567;

(c) a DNA that encodes a fragment of a peptide encoded by the sequences of (a) or (b), which fragment is capable of binding IL-15;

(d) DNAs that hybridize to the DNA sequences of (a), (b) or (c) or their complementary strands under conditions of moderate stringency (50° C., 2×SSC), and which encode a polypeptide capable of binding IL-15; and (e) DNAs that, due to degeneracy of the genetic code, encode a polypeptide encoded by any of the foregoing DNAs.

5. An isolated DNA sequence according to claim 3 that encodes a human IL-15R.

6. An isolated DNA according to claim 1, encoding a modified IL-15R polypeptide having one or more changes in a primary amino acid sequence, which changes are selected from the group consisting of: inactivated N-linked glycosylation sites; modified KEX2 protease cleavage sites; deleted cysteine residues; and conservative amino acid substitutions, wherein the modified polypeptide binds IL-15.

7. A recombinant expression vector comprising a DNA according to claim 1.

8. A recombinant expression vector comprising a DNA according to claim 4.

9. A recombinant expression vector comprising a DNA according to claim 5.

10. A process for preparing an IL-15 receptor (IL-15R), comprising culturing a host cell transformed or transfected with a recombinant expression vector according to claim 7 under conditions promoting expression, and recovering a polypeptide from the culture, wherein the polypeptide is capable of binding IL-15.

11. A process for preparing an IL-15 receptor (IL-15R), comprising culturing a host cell transformed or transfected with a recombinant expression vector according to claim 8 under conditions promoting expression, and recovering a polypeptide from the culture, wherein the polypeptide is capable of binding IL-15.

12. A process for preparing an IL-15 receptor (IL-15R), comprising culturing a host cell transformed or transfected with a recombinant expression vector according to claim 9 under conditions promoting expression, and recovering a polypeptide from the culture, wherein the polypeptide is capable of binding IL-15.

* * * * *